(12) United States Patent
Pariseau

(10) Patent No.: US 12,379,362 B2
(45) Date of Patent: Aug. 5, 2025

(54) NETWORKED AIR QUALITY MONITORING SYSTEM

(71) Applicant: Particles Plus, Inc., Stoughton, MA (US)

(72) Inventor: David Pariseau, Los Altos, CA (US)

(73) Assignee: Particles Plus, Inc., Stoughton, MA (US)

( * ) Notice: Subject to any disclaimer, the term of this patent is extended or adjusted under 35 U.S.C. 154(b) by 70 days.

(21) Appl. No.: 17/407,855

(22) Filed: Aug. 20, 2021

(65) Prior Publication Data

US 2022/0178897 A1    Jun. 9, 2022

Related U.S. Application Data

(63) Continuation of application No. 16/556,074, filed on Aug. 29, 2019, now Pat. No. 11,112,395, which is a (Continued)

(51) Int. Cl.
*G01N 33/00* (2006.01)
*F24F 11/30* (2018.01)
(Continued)

(52) U.S. Cl.
CPC .......... *G01N 33/0075* (2013.01); *F24F 11/30* (2018.01); *G01N 1/2273* (2013.01); *F24F 2110/50* (2018.01)

(58) Field of Classification Search
CPC ........ F24F 11/0017; F24F 11/30; F24F 11/62; F24F 2110/50; G01N 1/2205; G01N 1/2273; G01N 15/0205; G01N 15/06; G01N 15/0612; G01N 15/1459; G01N 21/4788; G01N 21/53; G01N 33/00; G01N 33/0034; G01N 33/0075; G01N 35/00732; G01N 35/00871; G01N 2001/021; G01N 2015/0046; G01N 2015/0277;
(Continued)

(56) References Cited

U.S. PATENT DOCUMENTS 8,146,376 B1 *  4/2012  Williams ................. F24F 11/39
                                                            236/46 C
8,762,060 B2    6/2014  Chainer et al.
(Continued)

FOREIGN PATENT DOCUMENTS

CN    104535465 A    4/2015
WO    2015/160830 A1  10/2015
WO    2017/064376 A1  4/2017

OTHER PUBLICATIONS

Golczewski et al., Performance Modelling and Response of the Dual-wavelength Optical Particle Spectrometer (DWOPS). Abstracts of the European Aerosol Conference. 2004, pages S839-S840.
(Continued)

*Primary Examiner* — Stephen R Burgdorf
(74) *Attorney, Agent, or Firm* — McCarter & English, LLP

(57) ABSTRACT

A networked air quality monitoring system. Such a system could provide information beyond the user's local instrument on air quality over a much larger area. This information could be used by a user to make decisions about frequenting particular areas based on the results, or to alert them to changing conditions in the area so that the user might act before local conditions change.

16 Claims, 13 Drawing Sheets

Related U.S. Application Data continuation-in-part of application No. 15/442,611, filed on Feb. 24, 2017, now Pat. No. 10,810,869.

(51) Int. Cl.
*F24F 110/50* (2018.01)
*G01N 1/22* (2006.01)

(58) Field of Classification Search
CPC ... G01N 2015/0693; G01N 2015/1493; G01N 2035/00881; G01N 2035/0811; G02B 27/0006; G02B 27/126; G05B 19/0425; G05B 23/0294; G08B 17/107; G08C 25/04; Y02B 30/70
USPC .................................................. 340/870.06
See application file for complete search history.

(56) References Cited

U.S. PATENT DOCUMENTS

| | | | |
|---|---|---|---|
| 9,140,638 B2 | 9/2015 | Pariseau et al. | |
| 9,140,639 B2 | 9/2015 | Pariseau | |
| 9,141,094 B2 | 9/2015 | Pariseau et al. | |
| 9,157,847 B2 | 10/2015 | Pariseau et al. | |
| 9,158,652 B2 | 10/2015 | Pariseau | |
| 9,216,509 B2 | 12/2015 | Renkis | |
| 9,424,598 B1 | 8/2016 | Kraft | |
| 9,677,990 B2 | 6/2017 | Pariseau et al. | |
| 10,139,384 B1* | 11/2018 | Nourbakhsh | G01N 33/0075 |
| 10,292,055 B2 | 5/2019 | Carpenter et al. | |
| 10,810,869 B2 | 10/2020 | Pariseau | |
| 10,928,297 B2 | 2/2021 | Novosselov et al. | |
| 11,112,395 B2 | 9/2021 | Pariseau | |
| 2001/0029535 A1* | 10/2001 | Hirano | H04L 67/02 709/224 |
| 2002/0144537 A1 | 10/2002 | Sharp et al. | |
| 2003/0051023 A1 | 3/2003 | Reichel et al. | |
| 2005/0190058 A1* | 9/2005 | Call | G08B 21/12 356/417 |
| 2006/0027677 A1 | 2/2006 | Abts | |
| 2008/0146892 A1 | 6/2008 | LeBoeuf et al. | |
| 2008/0200181 A1 | 8/2008 | Zill et al. | |
| 2009/0095054 A1* | 4/2009 | Groves | G01N 15/0227 73/31.01 |
| 2010/0030382 A1 | 2/2010 | Shalat et al. | |
| 2010/0160744 A1 | 6/2010 | Ha et al. | |
| 2010/0257543 A1 | 10/2010 | Dvir et al. | |
| 2010/0303339 A1 | 12/2010 | Caduff | |
| 2011/0294517 A1 | 12/2011 | Hahm et al. | |
| 2013/0038470 A1 | 2/2013 | Niemeyer et al. | |
| 2013/0086615 A1 | 4/2013 | Williams et al. | |
| 2013/0340501 A1* | 12/2013 | Peacock | G01N 15/06 73/31.07 |
| 2014/0135040 A1* | 5/2014 | Edge | G01C 5/06 455/456.6 |
| 2014/0207282 A1* | 7/2014 | Angle | B25J 13/006 901/1 |
| 2014/0309782 A1 | 10/2014 | Sharpe et al. | |
| 2015/0077737 A1* | 3/2015 | Belinsky | G01N 15/0211 250/208.2 |
| 2015/0212057 A1 | 7/2015 | Darveau | |
| 2015/0228171 A1* | 8/2015 | Aebersold | G08B 17/107 340/630 |
| 2016/0014566 A1 | 1/2016 | Bengtsson et al. | |
| 2016/0066068 A1* | 3/2016 | Schultz | F24F 11/523 340/870.07 |
| 2016/0153884 A1 | 6/2016 | Han et al. | |
| 2016/0252452 A1* | 9/2016 | Thun | G01N 15/0211 356/51 |
| 2016/0378109 A1 | 12/2016 | Raffa et al. | |
| 2017/0039235 A1 | 2/2017 | Benrachi et al. | |
| 2017/0241893 A1* | 8/2017 | Walls | G01N 15/0205 |
| 2017/0315103 A1 | 11/2017 | Biswas et al. | |
| 2018/0010935 A1 | 1/2018 | Amott et al. | |
| 2018/0082566 A1 | 3/2018 | Semanoukian et al. | |
| 2018/0149590 A1* | 5/2018 | Erdtmann | G01N 21/53 |
| 2018/0299418 A1 | 10/2018 | Poincelet et al. | |

OTHER PUBLICATIONS

Juranyi et al., Dual-wavelength light-scattering technique for selective detection of volcanic ash particles in the presence of water droplets. Atmos Meas Tech. 2015;8:5213-5222.

Nagy et al., Numerical and experimental study of the performance of the dual wavelength optical particle spectrometer (DWOPS). Aerosol Science. 2007;38:467-478.

U.S. Appl. No. 15/442,611, filed Feb. 24, 2017, U.S. Pat. No. 10,810,869, Issued.

U.S. Appl. No. 16/556,074, filed Aug. 29, 2019, U.S. Pat. No. 11,112,395, Issued.

* cited by examiner

AirQuality Instrument Type
- Sensor Id#
- Sensor Name
- List of integrated sensors
- List of installed sensors
- Details on each sensor
  - Sample rate
  - Sample volume
  - Parameter type
  - Parameter accuracy
  - Parameter resolution
  - Parameter range
  - Temperature range

401

Sample air quality data record 411

| Air quality instrument | Attached sensor List | Annotation |
|---|---|---|
| - AQ instrument type<br>- Unique Id#<br>- Current Date/time<br>- Current Position | - Sensor Type<br>- Sensor Status<br>- Sensor Data | - Text notation<br>- Special Tag<br>- Media notation |
| 412 | 413 | 414 |

FIG. 4

NETWORKED AIR QUALITY MONITORING SYSTEM

This application is a continuation application of U.S. application Ser. No. 16/556,074, filed Aug. 29, 2019, which will issue Sep. 7, 2021 as U.S. Pat. No. 11,112,395, which is a continuation-in-part of U.S. application Ser. No. 15/442,611, filed Feb. 24, 2017, which issued Oct. 20, 2020 as U.S. Pat. No. 10,810,869, the entire contents of the above application being incorporated herein by reference.

BACKGROUND

Field of the Invention

The present invention is related to instruments within systems and, more specifically to air quality monitoring instruments within systems.

Background of the Invention

With the increase in miniaturization, portable and wearable electronic products are a growing trend. As such, sophisticated air quality monitoring instruments are increasingly within reach of individual users. Such instruments, however, have a limited range and can only measure conditions in the immediate vicinity of the instrument. Air quality is of increasing concern for individuals. Numerous studies have been published linking air quality with short and long term health problems. For example: The World Health Organization WHO estimates that some 80% of outdoor air pollution-related premature deaths were due to ischaemic heart disease and strokes, while 14% of deaths were due to chronic obstructive pulmonary disease or acute lower respiratory infections; and 6% of deaths were due to lung cancer.

Ambient outdoor air pollution in both cities and rural areas was estimated to cause 3.7 million premature deaths worldwide per year in 2012; this mortality is due to exposure to small particulate matter of 10 microns or less in diameter $PM_{10}$, which cause cardiovascular and respiratory disease, and cancers.

The 2005 "WHO Air quality guidelines" offer global guidance on thresholds and limits for key air pollutants that pose health risks. The Guidelines indicate that by reducing particulate matter $PM_{10}$ pollution from 70 to 20 micrograms per cubic meter µg/m3, we can cut air pollution-related deaths by around 15%.

The Guidelines apply worldwide and are based on expert evaluation of current scientific evidence for:
 particulate matter (PM)
 ozone ($O_3$)
 nitrogen dioxide ($NO_2$); and
 sulfur dioxide ($SO_2$), in all WHO regions.

In addition to the above, a number of other parameters affecting health are also cited by other sources like the Centers for Disease Control CDC. These include Carbon Monoxide. Lead, Nitrogen Oxide, Acrolein, Asbestos, Benzene, Carbon Disulfide, Creosote, Fuel oils like Kerosene, Polycyclic Aromatic Hydrocarbons, Synthetic Vitreous Fibers, Total Petroleum Hydrocarbons. Various other volatile organic compounds like Formaldehyde are also of interest since products manufactured with these are present in some countries. Therefore, what is needed is system that monitors air quality in a given geographical area and provides information about air quality for the given geographical area to a user.

SUMMARY

A crowdsourced air quality monitoring system is disclosed in accordance with the various aspects and embodiments of the invention. The system monitors air quality in a given geographical area and provides information about the air quality for the given geographical area to a user. The system includes at least one air quality monitoring instrument and a server that is communication with the instrument. The instrument includes at least one air quality sensor and connects to the server through a network. The system monitors air quality and air quality information, including at least one of a current date, a time, and a position, is communicated from the instrument through the network to the server.

Preferred embodiments utilize a plurality of geographically distributed sensor devices that can include one or more optical particle counters to provide quantitative particle count data that is processed to map a geographic distribution of measured amounts of selected airborne particles.

The system can utilize bi-directional communication to control operation of the airborne particulate sensors that are geographically distributed in a region to be monitored. The system can use one or more controllers that can remotely control operating parameters of the individual sensor devices and also control geographic position or communicate with users of sensor devices to direct movement and operation of such sensors.

The control system can utilize one or more feedback control programs wherein the sensed data, processed data or aggregated data to adjust operating parameters such as temporal sensing period, sleep cycle or onboard processing function or to move automatically to different locations. A preferred embodiment can use a server running programmable software module to operate the system. Further embodiments can utilize either an algorithm engineered or derived through machine learning or other computational methods to direct a "fleet" of sensors in real-time in an environment to perform mapping of air quality based on feedback from the sensors. The server itself can reside in the cloud, or can reside in one or more remote locations and simply use the cloud to route traffic to and from the sensors.

Embodiments employ an intelligent system that can address a broader mandate and that can manage a fleet of sensors that can be deployed on various tasks and regions that react in real-time to variances in the environment during data collection to provide the best coverage and data possible in a cost-effective manner.

Embodiments are for outdoor air quality monitoring but this also applies to similar missions for indoor monitoring where the fleet of sensors can be located on humans, robots, drones, etc. moving through an enclosed space and mapping air quality within that confined environment. A large factory (perhaps an automotive plant) can have multiple sources of potential airborne contamination that can impact air quality throughout the plant. Monitoring air quality and identifying sources of contamination that led to events of elevated particulate levels, can protect workers, reduce potential liabilities and perhaps even improve production quality/yields by keeping particulates from contaminating products or processes.

Many large sites like campuses, industrial/manufacturing concerns or municipalities, etc. implement air quality monitoring either with large numbers of sensors placed in fixed locations, or with a smaller number of sensors used to provide audits (periodic or not) of the air quality in the region of interest. Some manufacturers are contractually required by the municipalities where they reside to provide fence line or perimeter monitoring of their sites to ensure that the air passing through the facility and leaving the site meets or does not exceed agreed upon levels. Even if there is no direct contractual obligation, many such sites monitor air quality to provide early warning of any issues and also to potentially limit liability. In larger sites the perimeter can be large such that a significant number of fixed sensors are required to provide reasonable monitoring of air quality over its entire length. These are expensive to install and maintain and a lot of data points must be regularly monitored and managed. In the case of an event, there might still not be enough sensors in the desired area to provide acceptable resolution. Making changes to such a network to account for changes in the site or monitoring requirements is difficult and expensive.

Campuses or municipalities must cover a large geographic area (in the case of municipalities a much larger area). And, this is sometimes done with a few fixed sensors, (often of varying quality) or by taking a few mobile sensors and performing some type of fixed audit (the latter being in response to a complaint or concern). These systems are often custom solutions derived by consultants to capture data and provide some reports and are seldom very flexible or have the features to address a variety of situations where dynamic data would be advantageous.

With fixed monitoring or even with unguided mobile audits, it can be difficult to identify the source of local airborne contamination within a site or region. Data from the sensors is typically collected over some period and then analyzed offline to attempt to build a geographic picture of the air quality over the area in question and infer sources. Mobile audits are at the mercy of conditions at the moment they are performing the audit and the specific locations where the measurements are made. It can be very challenging to unambiguously identify contamination sources from the data or to provide enough detail to infer the actual contamination levels at the source. And, since audits can seldom be timed to coincide with contamination events (that are not constant) many events likely go undetected. And, since reducing local sources of contamination can play a huge role in overall air quality for an area, detecting such sources and levying appropriate fines can have a huge impact in deterring such events and improving overall air quality while providing a significant revenue stream for these efforts and others within a municipality.

Preferred embodiments provide a controlled plurality "fleet" of mobile air quality sensors. Fleet is meant to convey that these sensors are largely mobile, though there might be a number of fixed sensors within the environment that provide early warning and prompt the deployment of the mobile fleet to investigate. Examples of such fleets include pedestrians, vehicles, robots, drones, etc.

The data from these sensors can be formatted to include:
geographic location (i.e. GPS or equivalent),
air quality metrics (particulate concentrations, particulate mass. VOC, CO2, other gases, etc.)
and it might also include environmental information (temperature, humidity, air velocity and direction, etc.)

Though the data can be stored locally in the sensors, the geographic location and air quality information (and environmental information if present) is transmitted to one or more servers either in the cloud or via the cloud or cellular network, for example. And, that the system (i.e. the server(s) connected to the fleet of sensors via the cloud) can direct the motion of at least some these sensors in real-time to optimize the mission in question (or perhaps change it altogether).

The cloud-based system can function using fixed pre-defined algorithms but it can also implemented using artificial intelligence processing system whereby a computational method is used to interactively compute a metric based on the measured data provided at one or more selected temporal intervals. The computational method can be structured to minimize a selected metric, which can be a particle size and/or mass measurement error metric, for example.

A further application of machine learning methods can be applied to generate improved geographic mapping of air quality information by utilizing real time weather data including wind velocity and precipitation data over the particle detection spatial region. Weather radar data can be used, for example, to improve the particle data distribution and/or machine learning to deriver or refine algorithms over time and thus optimize sensor motion. In this way the data collection can be tailored to provide the best coverage given the current conditions (air velocity/direction, location, and air quality).

Such a system can be autonomous in that based on some fixed sensors or non-directed sensors or a small number of periodic audits with directed sensors can monitor general air quality conditions and if some of the air quality parameters being monitored exceeded some minimum threshold, a larger fleet of sensors can be deployed to that specific area to investigate and map the event in much finer detail than is possible with a fixed installation of sensors or even a pre-defined grid route of mobile sensors.

As each sensor reported current local conditions, the system can use the aggregated information to reposition some or all sensors in the fleet to contour and map the event, ideally arriving at the event's source. And, once there, the source can be monitored in high-resolution with multiple sensors in order to provide a much more accurate measure of the air quality impact. In the case of municipalities this can provide them with a much more effective means of managing their air quality and citing/fining offenders, which is a significant source of revenue and a deterrent (helping to improve long-term air quality for the municipalities).

In the case of border or boundary monitoring, a small fleet of sensors monitors a very large area, and if equipped with wind direction and velocity information, then only a small region of the boundary line is monitored (just the air leaving the perimeter), further reducing the required fleet. With this system directed from a central controller the fleet can be managed and relocated in real-time to adjust to varying conditions. In the case of an event a larger number of sensors can be deployed to monitor and map it, while some of the sensors can be tasked with quickly identifying and then monitoring the source of the event within the site.

The system can be tasked for a number of missions, and these can be changed dynamically. Provide periodic monitoring (1 minute every 15 minutes) of this fence line, optimizing for points in the path of the current wind direction. If the air quality on any point is above threshold X (75 ug/m3, TVOCs>100 ppb, etc.) then triple monitoring density with points (continuous 1 minute samples) until threshold falls for 1 hour, and map the contour, and deploy sensors to identify the source(s) and map/monitor it/them (continuous 1 minutes samples). The monitoring period can be manually or automatically adjusted based on the sensed conditions, and is preferably 1 hour or less, 15 minutes or less, five minutes or less depending upon the particular environmental conditions.

This can be setup through menu selections or natural language or through machine learning with user feedback where the system evolves its own improved set of mission guidelines. The general guidelines provide intelligent monitoring system that can manage the entire fleet of sensors to implement all of the monitoring required under a wide range of conditions. The system can also be instructed to prepare analyses or reports based on the above and escalate such should conditions warrant it, so that appropriate actions can be taken in those cases.

In the case of a disaster, a fleet can be deployed in the area with a few simple directives to the system, to identify the source or monitor an area of it or contour it or any number of such missions.

As noted above, a fleet is a generic term and the mobility can be provided in a large number of ways, some of which are below. In each case the system can direct the sensors in the fleet to follow a real-time path and collect the air quality, location and perhaps other environmental data (air velocity, direction . . . ):

a) Pedestrians with cloud-access (e.g., smartphones) can be directed via a map on it and either collect the data continuously as they are moving or stop and take samples of varying length when directed, b) Pedestrians with cloud-access (possibly cellular) can be directed via an onboard map and either collect the data continuously as they are moving or stop and take samples of varying length when directed, c) Robots with cloud-access (possibly cellular) can be directed via an onboard map or waypoints and either collect the data continuously as they are moving or stop and take samples of varying length when directed.

d) Drones with cloud-access (possibly cellular) can be directed via an onboard map or waypoints and either collect the data continuously as they are moving or stop and take samples of varying length when directed, There can also be sensors that are part of mobile platforms that are connected in real-time through cloud-access but are NOT directed by the system. Many city vehicles, or even fleets of taxis or delivery vehicles, can be outfitted with such sensors and provide real-time data throughout the region as they go about their daily business navigating the area in question. Though such units might not be directly controlled by the system, they can provide valuable early-warning or the general monitoring information for the system. Their data can be sufficient for normal auditing or monitoring purposes, allowing the directed fleet to be held in readiness in the event its use is required or for an under-monitored area require some additional monitoring.

One implementation involves a sensor manufacturer or integrator developing the sensors and the transport for them (fleet) into an off-the-shelf integrated package. They might also develop the system software for managing and directing the sensors based on real-time algorithms or a machine-learning framework. The software can also incorporate the user-interface to provide management, scheduling, reporting, tasking, etc. Ideally this can all be provided and supported by a single firm to users who can deploy them with a minimum of training and support.

BRIEF DESCRIPTION OF THE DRAWINGS

The foregoing summary as well as the following detailed description is better understood when read in conjunction with the appended drawings. For the purpose of illustrating the invention, there is shown in the drawings exemplary embodiments in accordance with various aspects of the invention. However, the invention is not limited to the specific embodiments and methods disclosed. In the drawings:

FIG. 4 shows a table that includes an example of a configuration structure that might be used to describe an air quality instrument.

DETAILED DESCRIPTION

Figure 1:
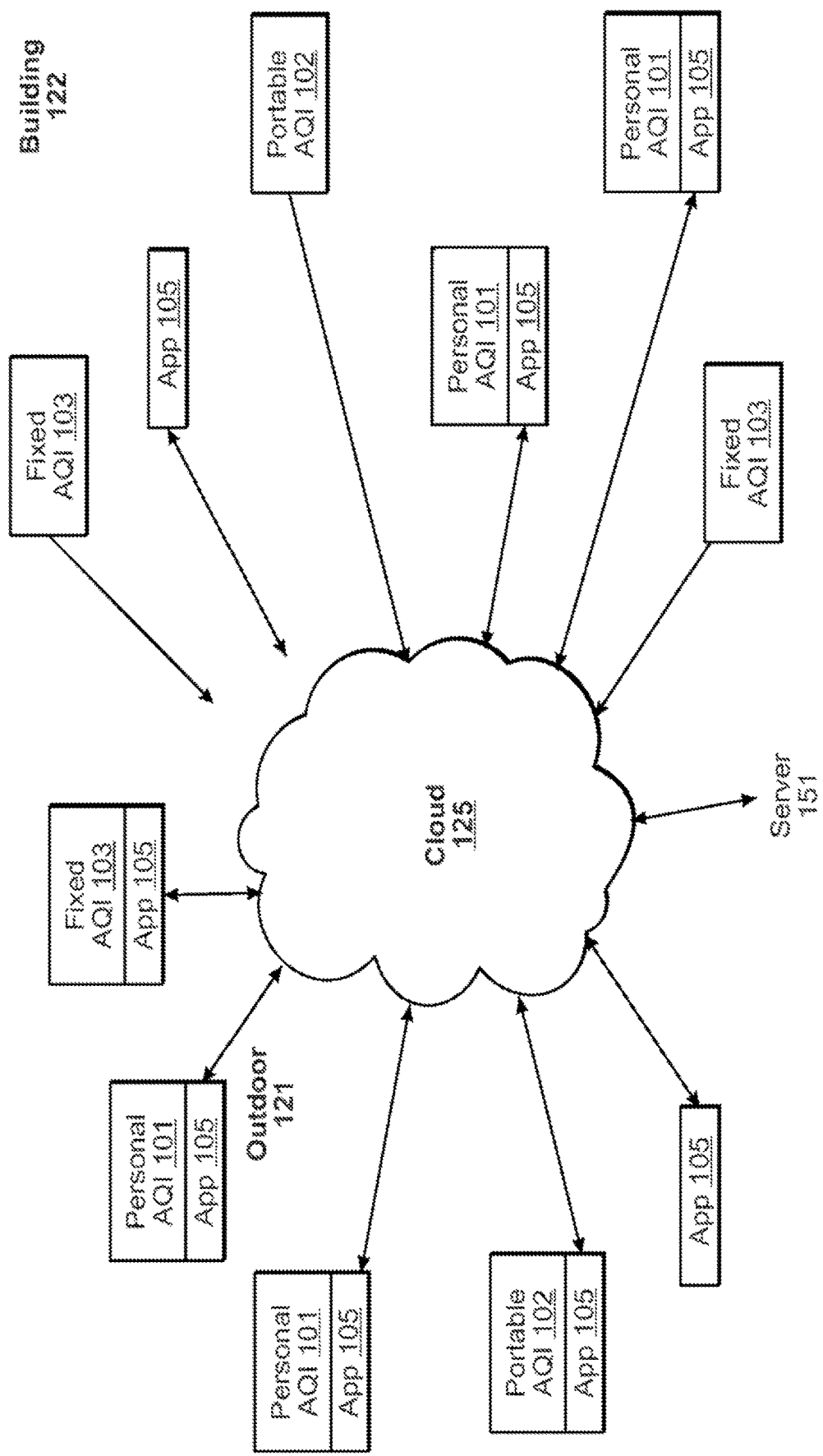
FIG. 1 is a crowdsourced air quality system in accordance with the various aspects and embodiment of the invention.

To the extent that the terms "including", "includes", "having", "has", "with", or variants thereof are used in either the detailed description and the claims, such terms are intended to be inclusive in a similar manner to the term "comprising". The invention is described in accordance with the aspects and embodiments in the following description with reference to the FIGs., in which like numbers represent the same or similar elements. Reference throughout this specification to "one embodiment," "an embodiment," or similar language means that a particular feature, structure, or characteristic described in connection with the various aspects and embodiments are included in at least one embodiment of the invention. Thus, appearances of the phrases "in one embodiment," "in an embodiment," "in certain embodiments," and similar language throughout this specification refer to the various aspects and embodiments of the invention. It is noted that, as used in this description, the singular forms "a," "an" and "the" include plural referents, unless the context clearly dictates otherwise.

The described features, structures, or characteristics of the invention may be combined in any suitable manner in accordance with the aspects and one or more embodiments of the invention. In the following description, numerous specific details are recited to provide an understanding of various embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring the aspects of the invention.

Where a range of values is provided, it is understood that each intervening value, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

All publications and patents cited in this specification are herein incorporated by reference as if each individual publication or patent were specifically and individually indicated to be incorporated by reference and are incorporated herein by reference to disclose and describe the methods and/or system in connection with which the publications are cited. The citation of any publication is for its disclosure prior to the filing date and should not be construed as an admission that the invention is not entitled to antedate such publication by virtue of prior invention. Further, the dates of publication provided may be different from the actual publication dates, which may need to be independently confirmed.

There is a distinction between the types of factors one is most concerned with for indoor air quality vs. outdoor air quality monitoring, for example for indoor air quality CO2 is of larger concern though CO2 is seldom an issue in outdoor air quality. Air quality monitoring instruments measure various parameters in proximity to the instrument. These parameters might include, but are not limited to particulates and/or various gases to create a picture of the local environment. In order to map out a larger area like a building for indoor air quality, or a city for outdoor air quality current systems if they exist rely on networks of fixed instruments. One or more computers collect the data from these instruments in order to determine the conditions in proximity to each and then attempt to represent the area from these. As noted, these systems are largely comprised of fixed systems and typically purchased and deployed by the system administrator.

An emerging class of applications are using crowdsourcing to collect and aggregate data. This has become popular for traffic reporting. Systems like Waze and others collect GPS and other data like notes or observations from individual users and then aggregate this data to provide a detailed view over a larger geographic area than any individual could otherwise construct. Also, these sensors are owned by the individuals not the system.

With the advent of the Internet-of-things (IOT) aggregating data from disparate sensors and making processed results available to end-users is a growing trend. This is facilitating the creation of the required infrastructure in order to make such an application possible. Prior to the existence of ubiquitous high-speed networks with low-cost chipsets and servers to process these creating such a system would have been a daunting prospect, and wouldn't have made practical sense.

Accordingly, a system of air quality instruments which are aggregated using crowdsourcing to produce an aggregate picture of air quality for use for indoor and/or outdoor air quality monitoring/reporting. Referring now to FIG. 1, a networked air quality system 100 is shown in accordance with the various aspects and embodiments of the invention.

FIG. 1 shows a hybrid system showing instruments and users in both an outdoor environment 121 and indoor environment, for example within a building 122. It also shows a mixture of air quality instruments, such as hand held or bodyworn personal instruments 101, portable instruments 102 and fixed air quality instruments (AQI) 103. Each instrument 101-103 can measure one or more air quality parameters which might include, but is not limited to: particulates. Temperature. Relative Humidity, CO2, CO, NO, NO2, SO2, O3, aggregate or specific VOCs. They would report this information along with current sensor date/time and current sensor position information to at least one server in a network. The data can be aggregated by the server 151. The aggregated data would be available to applications (App) 105 allowing them to represent current or historical aggregated views of the system's geographical area.

The data could be sent by some instruments through the cloud directly by the server 151 without requiring an application. For example, air quality instruments 102-103, which are shown connected directly to the cloud 125 without an application 105, show arrows in a single direction, indicating traffic moving to the server 151 without receiving aggregate information. This would be the case in the case of instruments that don't have a user interface and instead merely collect and report data.

The cloud 125 indicates at least one network linking the various components in a system. This network is a logical construct and might well be composed of various distributed networks running various protocols over different physical layers. An example of such a network can be the internet.

The air quality, date/time and position information sent from all the air quality instruments 101-103, through the cloud 125 would be collected by one or more servers 151 and aggregated to create an aggregate data set of the various air quality parameters across a geographic area. One or more servers 151 would make that aggregated data available to applications 105. These applications 105 could run on separate devices like personal computers, tablets, smart phones, etc. or within the air quality instruments themselves 101-103.

Figure 2:
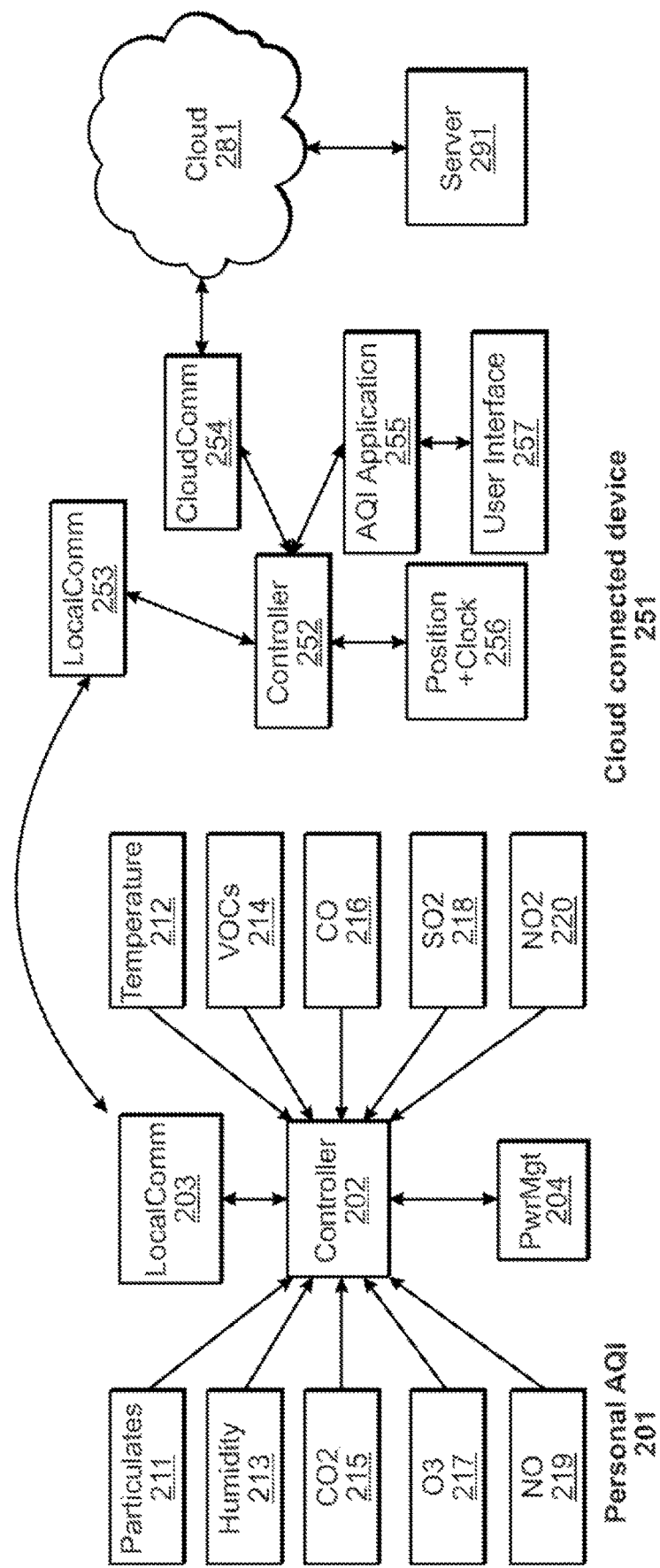
FIG. 2 is an implementation with a personal air quality instrument system in accordance with the various aspects and embodiment of the invention.

FIG. 2 shows an implementation with a personal air quality instrument 201 which comprises a number of air quality sensors 211-220, a local controller 202, power management circuitry 204 and a local communications controller 203. This instance happens to contain sensors 211-220, but other implementations might only have a subset of these or might incorporate other air quality sensors not shown. The intention is not to stipulate a specific sensor technology, for example the particulate sensor might be implemented as an optical particle counter (OPC) or it might be a photometer, or be based on some other technology. The various aspects and embodiment of the invention is directed at the overall system implementation and not limited by the details of the integration of the individual sensors that can be used in the implementation of the system.

The arrows in the diagram show information or signals moving from the various sensors to the local controller 202, but this is merely to indicate the direction of the air quality information. There can be bidirectional communication to these sensors in order to calibrate, configure, monitor or operate them. The local controller 202 collects air quality data from the sensors 211-220 and might condition, filter, linearize, offset and/or scale the data in order to provide information with standard units, or it might merely send raw data on for processing elsewhere in the system.

The power management circuitry 204 implements these features in the system, it might include voltage regulators, voltage references, current sources for some of the sensors battery management and/or charging, etc. The local communications controller 203 implements a local communication link, for example Bluetooth, or Zigbee, etc. to a cloud connected device 251. If the Local communications controller 203 has enough onboard resources it might even also be the local controller 202 for the instrument. The bidirectional interface between the personal AQI 201 and the cloud connected device 251 is concerned with gathering air quality information from the device as well as any status or error conditions, although the cloud connected device 251 might also control the operation of the air quality instrument 201, perhaps to switch between sleep/active modes or performing diagnostics or calibration.

Some implementations of the invention might merge the personal AQI portion 201 with the cloud connected device portion 251 to create a single integrated device. Such an implementation wouldn't require, though it might still contain, either local communications controller 203, 253.

The cloud connected device 251 would typically be an off-the-shelf though it could be custom device like a smartphone, a tablet, or a laptop, etc. An application 255 running either locally on the controller 252 or partially from the web, in the case of a web-based application would gather air quality and status information from the AQI 201 as well as position and date/time information from the position/clock sensor 256 on the cloud connected device 251 and would send this information using the cloud communications controller 254 through the cloud 281 to Server 291. The application 255 can also receive aggregated data or visual representations of the data like maps over the same link and can display such with its local data on its user interface 257. The cloud 281 could be any network, wireless or wired, and the server 291 any type of computer or instrument that can be used to collect and store the incoming data, and serve aggregate data back to the client applications 255.

The user interface 257 might take several forms, in addition to a traditional display with a touchscreen, it might well involve simple SMS type messages to a phone to indicate air quality status either locally or in the geographic environment, or it might simply involve beeping or vibrating. Some cloud connected devices 251 might not have any user interface at all, and could merely be reporting air quality, status, date/time, and position information without requesting any aggregate data or results.

One particular case of the above might involve a sensor network which might be deployed in an area, perhaps as part of a response to some environmental event. For example, in the aftermath of some event sensors could be supplied to first responders, these would likely have associated displays as previously discussed. But, there might also be additional sensors attached to drones or even small robots moving through the area. In these cases, aggregate map information is not required by these devices, so the information flow for these instruments would be largely unidirectional with these instruments reporting their air quality, status, date/time, and position information, but having no need to receive aggregate data or results.

To further increase the sensor density a sensor network could be deployed. Simple air quality sensors in an area might all be connected to a local sensor network which in turn might be connected to the cloud. In such a system, the sensors themselves might only have simple local communications capabilities and lack accurate position information. In such cases the position of the cloud connected device 251 could be used to provide a proxy location for the various sensors in the local sensor network and this data for these sensors could be listed or averaged, or perhaps shown with both average and standard deviation.

Another alternative would be to derive the individual sensor locations from the sensor network and have a local controller fill in the derived position and attach it with the current date/time to the air quality information before forwarding that on to the server. This allows each individual sensor to be much lower-cost, and hence allow for the deployment of larger number of these.

Figure 3:
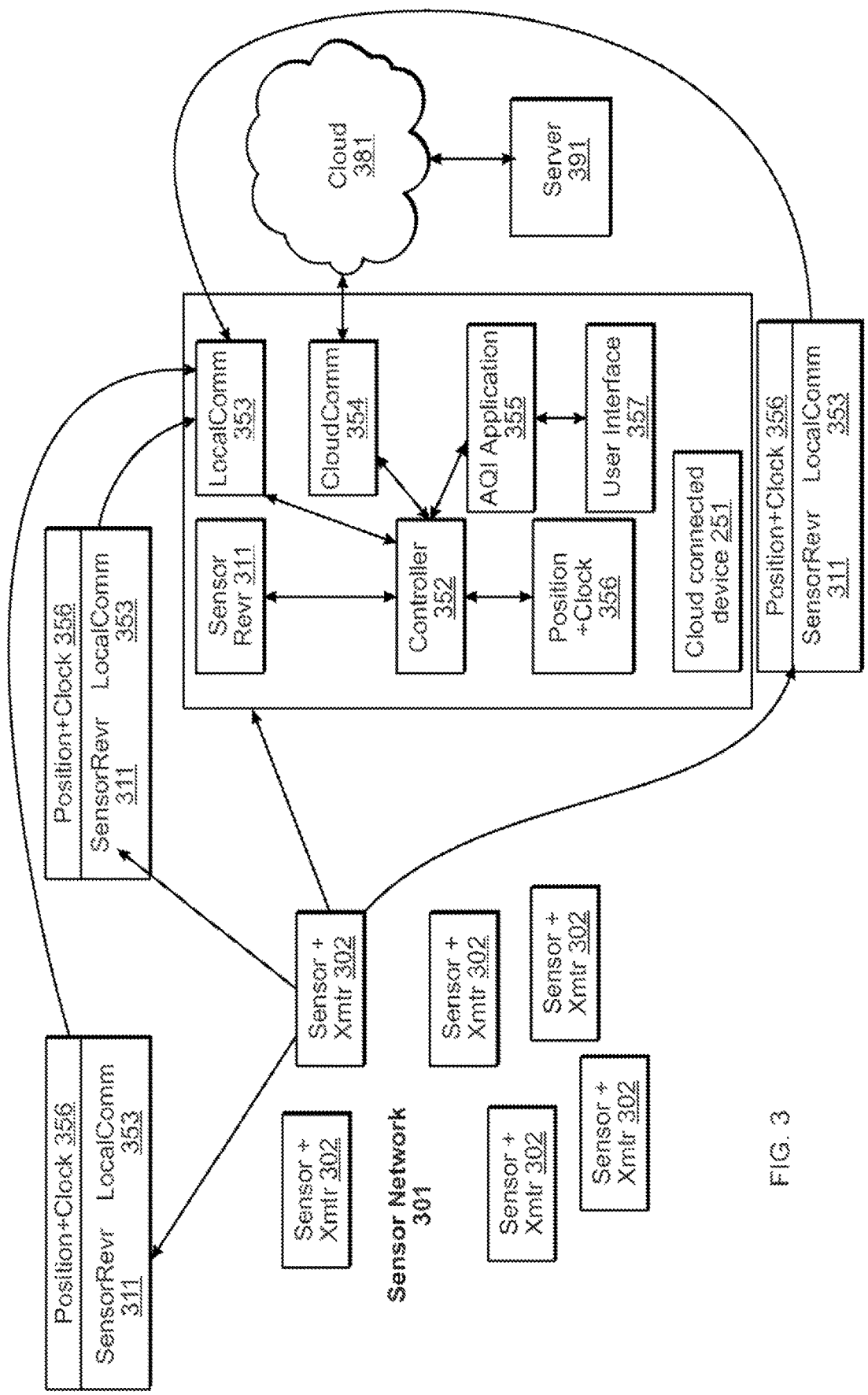
FIG. 3 shows a network of air quality sensors in accordance with the various aspects and embodiment of the invention.

Referring now to FIG. 3, such a network is shown. A number of air quality sensors 302 would be released and move about the environment or be strewn throughout the environment perhaps dropped by air using a drone. These sensors 302 would have one or more onboard air quality sensors and at least one short-range communications transmitter though they might also have receivers, discussed later. These sensors 302 would comprise a sensor network 301. Each sensor 302 would periodically report air quality information from their sensors using their integrated transmitters.

A small number of sensor receivers 311, with precise clocks and position sensors 356 would timestamp these received messages and communicate such within a local network using their integrated local communications controllers 353. From this information, a local controller, in this case the cloud connected device 351, could determine the position of the sensors and attach that position information along with the current date/time to the air quality information received from the sensor 302. The position information would be determined by triangulation with 3 sensor receivers 311 providing enough information to determine relative position in 2 dimensions, and 4 sensor receivers 311 providing enough information to determine relative position in 4 dimensions for example, like GPS. Since each sensor receiver 311 would also have accurate position information due to their local position sensor 356 the relative position of the sensors could be converted to an absolute position.

Once position information is derived, that information can be attached to the sensor air quality information and then communicated via a cloud connected device 351 via its cloud communications controller 354 through a network cloud 381 to at least one server 391. This would allow for a large number of low-cost air quality sensors 302 to be deployed with a minimum of electronics.

The arrows from the sensor nodes 302 and from the local communications controllers 353 are drawn as unidirectional to show the main direction of the sensor information. However, all devices 302 and 311 on the sensor network could have both transmitters and receivers to enable bidirectional communications. This allows for calibration and configuration information to flow. It can also allow the system to provide direction information to the various sensors 302 in order to more evenly deploy or direct them perhaps redeploying them based on changing conditions within an environment and also keep them within the desired area.

A key differentiator of this invention is that the air quality information is closely coupled with current date, time, and position information for that instrument. The position information is deemed to be dynamic and is recorded if not with every record then at a sufficient rate to record changes in position. This information is used to create a dynamic aggregate map of air quality conditions across a geographic area. And, though in some cases, gross location information is included in some monitoring systems, it is not intended as geographic coordinates but rather as informational location markers like "Gowning Room Vent" or "Lithography door" or "Room 103 doorway" and such are typically stationary designators even if the instrument is sometimes moved and the location changed manually by a user.

In the case of fixed instruments our position information might be static, but it would still be communicated at least periodically with the air quality information. The position data might be sourced directly from a GPS receiver, but it might also be derived from a street address perhaps on installation and then communicated thereafter as the same derived position information. The system might have a field to indicate that this is a fixed location. Pulsed light ranging device can also be used to locate selected sensor devices.

In addition to position information, one or more annotation fields might also be included with the data. These fields might be used to provide additional location or status information to the air quality records. For example, an annotation field might be used to provide additional location information like "Starbucks" so that if annotations were included on a map the user would see then enhanced location information. In this way, a merchant had installed filtration equipment and was touting enhanced air quality might note the name of their establishment on a map.

Annotations might also enable users to add observations to the data attempting in order to provide context to the reported values. For example, a user might note that "Burning leaves" to provide some explanation for the increased particulate counts in a neighborhood. "Vehicle on fire on shoulder" might be provide context for elevated particulates on a stretch of freeway. Applications like Waze allow users to make comments about traffic issues they witness which provides context for users of the system in understanding the underlying causes of issues in the traffic and gauge how this might impact the data over time. So, similarly allowing users to make comments about leaf-blowers, pressure washers, dirty truck exhaust, traffic jams, etc. when air quality is compromised might add context to the raw information.

Since annotations are sent along with the normal data stream the current location is included they can be associated with a location where they were made as in the above examples. However, they could also be associated with a particular air quality instrument, and as such might include a particular identifier for each. This might be useful to track particular first responders within an environment by assigning each a tag and annotating it such that annotation is not persistent and is updated on the next sample from that instrument, as such the tag would then move with the air quality instrument, and be fixed at their last known position.

These annotations could also be configured in the system to have special functions. For example, special tags could be embedded within the annotations to provide special functionality. Such functionality might include a link to network addresses or URL that could be accessed from the user's map. Such a link might provide an advertisement for the establishment, or a promotional offer, or simply be a link to the website for a fixed location. The system implementer might well charge for the use of these special tags, creating a revenue stream from these.

The tags could also be media such as images or video. In that way, a picture, audio clip, or video of the current area or the user describing such could be attached to a sample and viewed by other system users.

In accordance with the various aspects and embodiment of the invention, number of different systems can be configured from the basic premise. For each of these, a number of business cases are possible. In accordance with the various aspects and embodiment of the invention, the system can be implemented as a public system, much like a Waze, providing public access to the system to all enrollees, which might be paid or free subscribers. In such a case, users could connect to the system by downloading an app or connecting to a web-based app and view the created aggregate maps from other users equipped with air quality instruments and connected to the system. If the user also has an air quality instrument, that instrument could also be connected to the system via the app to add their local data to the aggregate system data. Such a system would be available to all subscribers in good standing. With standing to be determined by the system administrators.

In accordance with the various aspects and embodiment of the invention, the system could also be implemented as a private system. It would allow, for example, for an entity to offer such a system distributed across a local area of concern and while making it accessible only to its members. For example, a university could implement such a system on a campus and make such a system available only to faculty and students. As such, annotations could also be used as public service announcements for the campus. The information stream could also be added to existing system to enhance it with air quality information. Likewise, a corporation can do the same for their campus, or even within one or more buildings.

In accordance with the various aspects and embodiment of the invention, the system can also be integrated within a facility management system with the data being used as an additional input for air handling and filtration systems. Thus, the filtration systems could respond to issues that might need to be addressed, but to which the system might otherwise be unaware. For example, alarm levels can be raised if personal air quality instruments worn by staff in a facility exceeded some aggregate ala-n level for an area. This might precipitate a response by staff to the areas in question, or it might even be integrated into an automated system to have an automatic response like increasing filtration or air changes to the areas in question.

In accordance with the various aspects and embodiment of the invention, the system is designed to track sensors that are in motion. This motion allows for a much better resolution with a small number of sensors. Since the sensors are in effect moving through an environment it produces many more data points within that area. It can take a large number of fixed sensors to produce an equivalent survey of the environment. Of course, the sampled data does not persist indefinitely, but producing models from historical data allows the aging of such data in the absence of new data. This aging of the sensor information could be represented on maps, perhaps by the varying the intensity of the entry, with older stale entries fading away over time.

Another possible feature is that the data combines indoor and outdoor air quality sensors and that the system might determine which of these environments is being measuring based on detailed positional data. So, if position puts a user within a building this can deem the data as originating indoor, or if the position puts the user on a sidewalk moving at a walking pace we could naturally assume that they are outdoors. This can also include assuming that the user is within a vehicle if they are on a freeway moving at 60 mph. Fixed sensors known to be located within buildings might simply always assumed to be indoors. Making this determination would allow the incoming data to be tagged as either indoor or outdoor. Aggregate data sets thus could allow the user to access only indoor or only outdoor data, or might allow them to have both types distinguished within a hybrid map, perhaps with unique symbols for each.

Another strength is that the sensors themselves can be quite disparate and purchased independently by the system users instead of by the entity managing the system. In this way, the system can grow quite quickly as personal air quality instrumentation becomes commonplace. Traditional monitoring systems are quite limited in scope and size due to the availability of instruments, with the bulk of these in fixed installations, typically capitalized by the system implementer.

When users connect to such a system and connect their air quality instruments to it, the connection or enrollment process would also identify the air quality instrument. Part of that identification would provide the specific details for the integrated sensors. This could include the types of sensors, what parameters they measure, their accuracy, resolution, how often they are sampled, what volume of air they sample, etc. This can be done by identifying the sensor as belonging to an air quality instrument already known to the system, or by detailing the details of some instrument by defining a new or custom instrument type, which would allow previously unknown instruments to be added dynamically to the system.

Referring now to FIG. 4, an example of a configuration structure 401, which might be used to describe an air quality instrument, is shown. Of course, much more information could be included like calibration or purchase date, user name identifier, etc. or some of the information could be excluded. The idea is merely that providing a central list of air quality instrument types for users to choose from can eliminate the need for a detailed technical description of these instruments and their capabilities to be made during the enrollment process. Instead the user can simply select from a list of available instruments. However, should the instrument not appear on the list, a mechanism can be available on the server to allow the user to add a new air quality instrument type to the list.

FIG. 4 includes a sample of an air quality instrument data record 411. That record has information on the sample in question 412 which includes the instrument type described above, a unique identifier for this instrument within the system, the date/time of the sample, and the position of the sample. To that is added the air quality instrument sensor information 413 which might include a list of the sensors, their status for that sample and their values for that sample. Finally, an annotation section 414 enables annotations to be added to that sample, as noted these might include simple text notation, special tags, or media notations.

In addition to allowing the aggregate display of the air quality over some user selectable geographic area, the application 105,255,355 could also display results from local air quality instrument 101,102,103,201 or sensor network 301. This allows the instrument to operate in local mode in the absence of a network for example on a plane.

The aggregate data displayed by the application 105,255, 305 could well include, as discussed, a geographic map of the local area. For indoor environments like buildings the map could be overlaid within a 3-D representation of the building in question if such were available as might well be the case for private networks. It could perhaps also be rendered automatically using available data for example, from Google Maps both overhead and street view for elevation and from GIS sources and then using position data which has altitude to determine a rough envelope for the building and then estimate the number of floors, etc.

Maps provide real-time information for the current air quality conditions but they could also provide historical information, where past air quality information would be available, perhaps to look at air quality over some previous period. Such data could be replayed, likely at an accelerated rate, to analyze or review the performance of a building over the course of normal use. It can be used to analyze propagation of events throughout an area over time, to perhaps then model and provide estimates for air quality events throughout an area based on events in proximity. Though map data is the most obvious usage of such a system there are other display options, including but not limited to, tabular lists, histograms, charts, etc.

Figure 11:
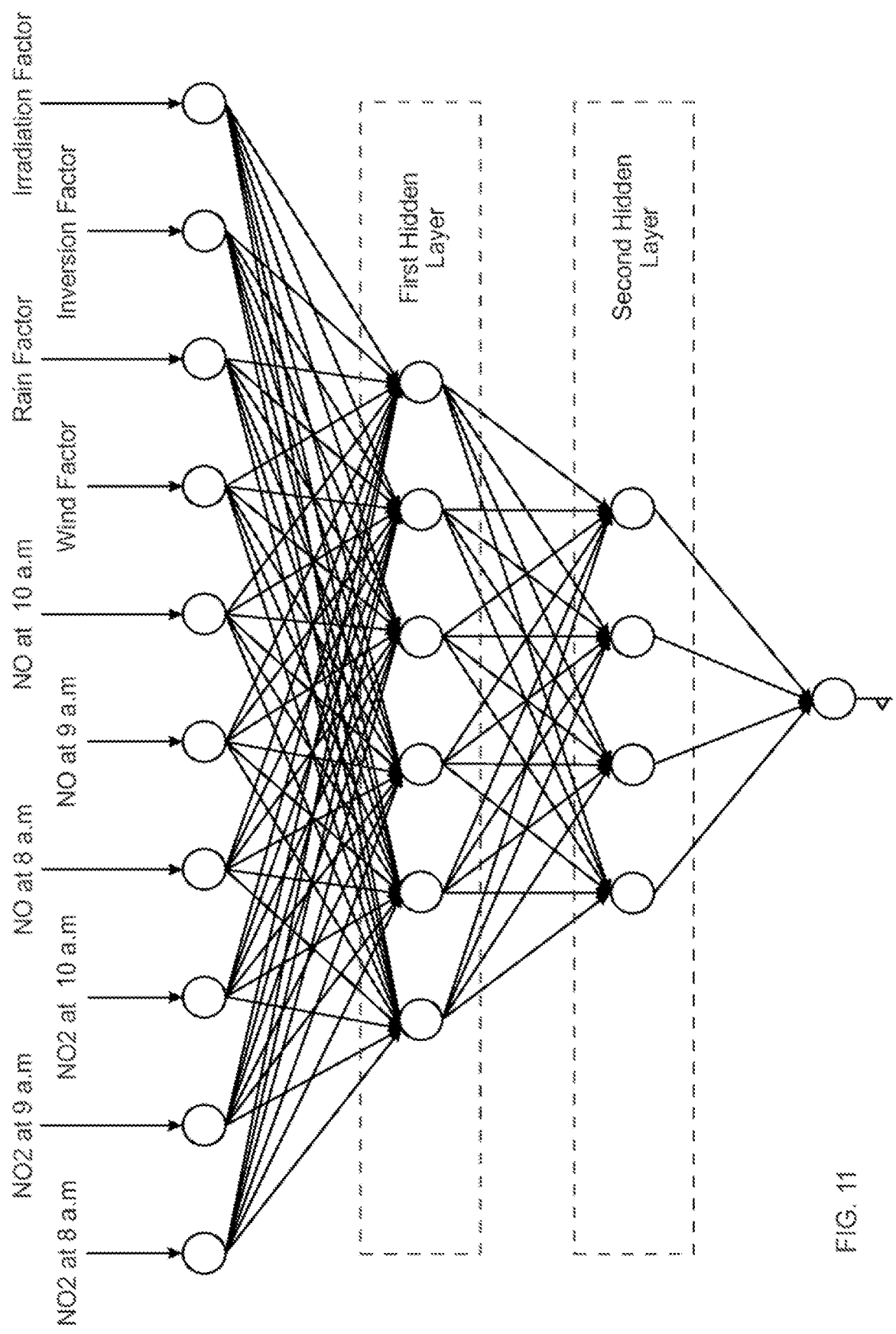
FIG. 11 illustrates an example of a neural network.
Figure 12:
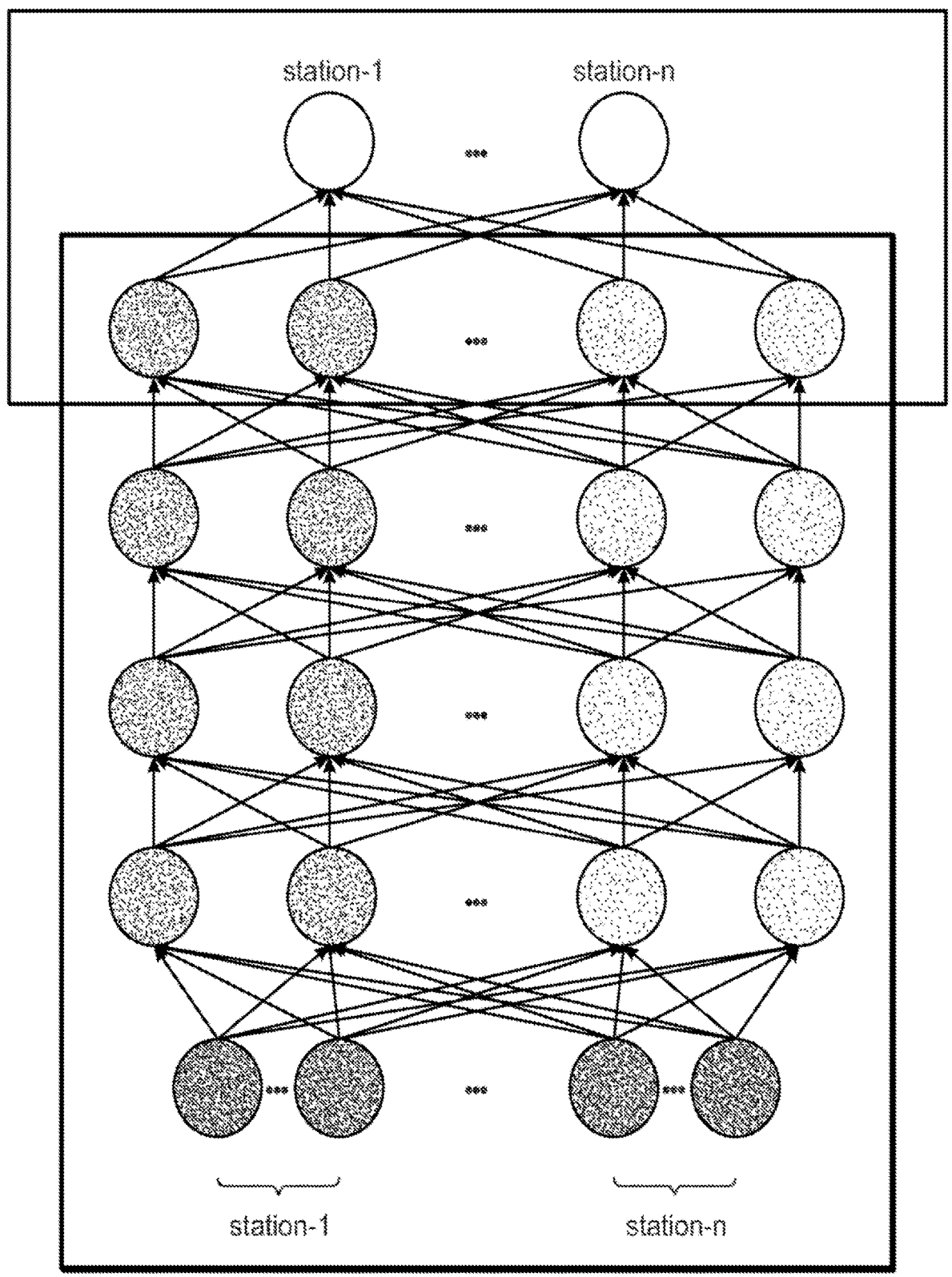
FIG. 12 illustrates an example of a support vector machine.

The maps themselves might become quite elaborate, allowing all air quality sensors to be displayed concurrently, or allowing only selected air quality parameters to be displayed. As noted, the sensor data could be aged through an area, perhaps delimiting an area of travel through an environment, like a comet trace with the head being the current position of the sensor and it being the most intense and the tail trailing along behind the head showing the path of travel and with the intensity declining to behind the head eventually to nothing. Perhaps the tail would vary in length and location based on factors like speed of travel, velocity of prevailing winds, etc. This can be useful in sparsely sensed areas, but in more densely sensed areas the display could significantly reduce the area for individual sensors and provide a more heavily aggregated view. The maps can have regions and sub-regions or can comprise a fixed grid enabling display of combined real time weather and air quality and particle count data as described herein. Techniques that can be used to process and aggregate data can include machine beaming application such computational regression techniques, neural networks (ANN) shown in FIG. 11, support vector machines (SVM) shown in FIG. 12 and hybrid computational methods using such implementation as described in "Air Quality Prediction; Big Data and Machine Learning Approaches, Kang, et al. International Journal of Environmental Science and Development, Vol. 9, No. 1, January 2018.

The historical aggregate data could be mined in order to create detailed environmental models or provide specific analyses. Though the data is available in map form for users, access to the aggregate data set can be sold separately to users interested in such creating an additional revenue stream.

The server 151.291.391, which could be a single server or a collection of servers located either centrally or distributed, would manage several functions. It would allow users to connect to the system, and manage the administration and creation of user accounts while controlling access. This would include allowing users to configure/attach new sensors to the system. A user might have one or more sensor associated with their account though users might be able to use the system without having any sensors. The account might be for an individual user, but it might also represent an entity like a corporation or academic institution. The sensors associated with the account would identify themselves through a unique identifier assigned by the server when adding the sensor to the system.

The server 151.291.391 can receive data from all connected air quality sensors 411. It would store this data and then periodically aggregate data into a current geographic dataset that would be used by the applications 105,255,355 to represent this aggregated data locally for the user, either in map form or in some other form.

In generating the aggregated current geographic dataset, the server 151.291.391 can factor in various parameters in order to create a more accurate model. This might include applying a weight to the value of the sensor data based on the accuracy of particular sensors, aging the sensor data, or factoring in outside information like meteorological sources, or historical or model based data.

The server 151.291.391 might also identify these sensors as either indoor or outdoor sensors, either from the configuration information defining a sensor as an indoor sensor located in a fixed location and/or from the position information and perhaps velocity and air quality information in comparison with other local sources whether that sensor is at the moment an indoor or outdoor sensor. Such a determination would allow applications 105,255,355 to display one dataset or the other or both, perhaps with some distinction in the representation identifying which type of sensor is represented in the case of a hybrid representation.

Figure 5:
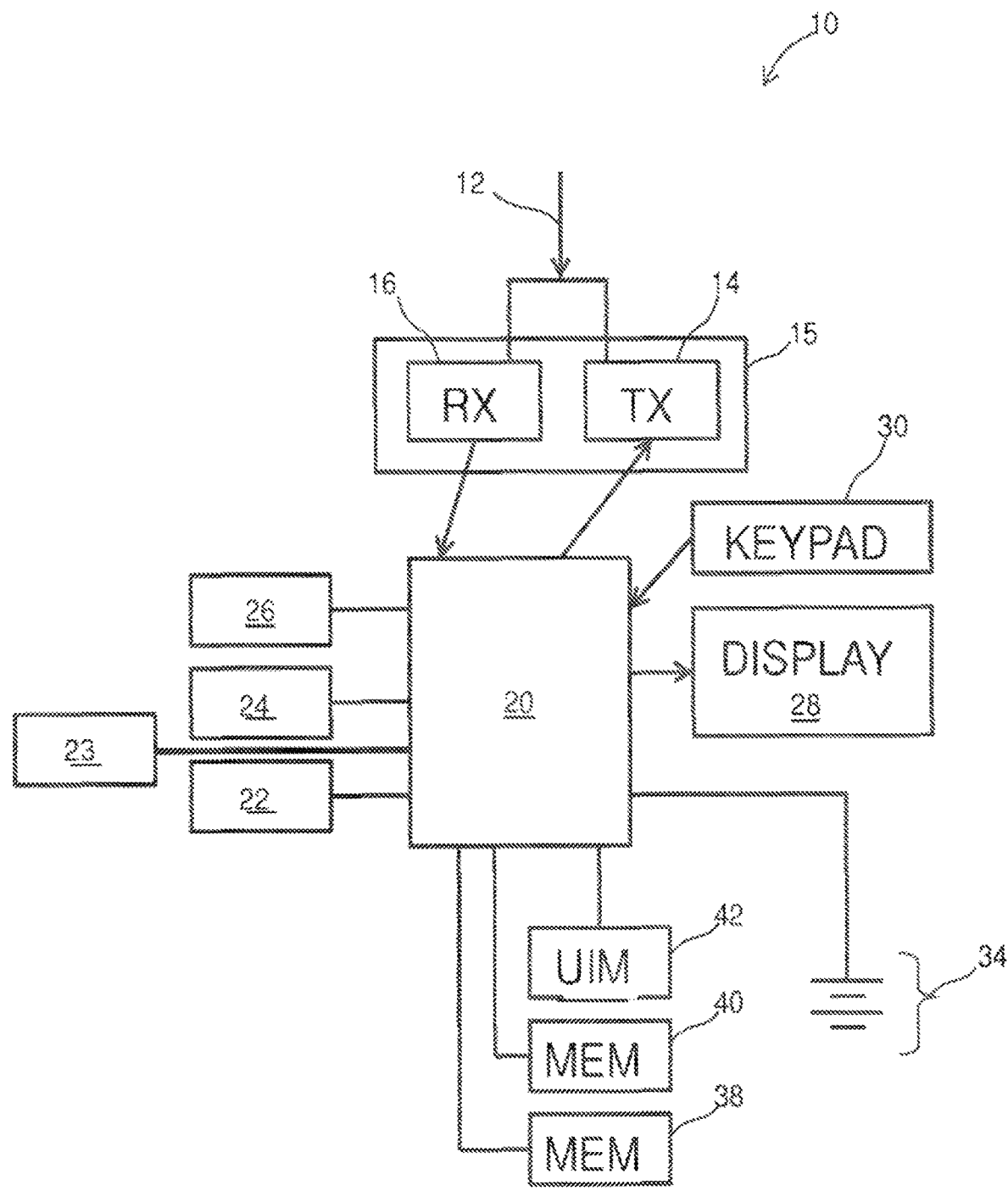
FIG. 5 shows a block diagram of a wireless communication device used in the various aspects and in at least one embodiment of the invention.

Referring to FIG. 5, based on the various aspects and embodiments of the invention, illustrates a block diagram of a wireless device 10, such as a mobile telephone or a mobile terminal. It should be understood, however, that the wireless device 10, as illustrated and hereinafter described, is merely illustrative of one type of wireless device and/or mobile device that would benefit from embodiments of the invention and, therefore, should not be taken to limit the scope of embodiments of the invention. While several aspects and embodiments of the wireless and mobile device are illustrated and will be hereinafter described for purposes of example, automobiles, other types of mobile terminals, such as portable digital assistants (PDAs), pagers, mobile televisions, gaming devices, laptop computers, cameras, video recorders, audio/video player, radio, GPS devices, or any combination of the aforementioned, and other types of voice and text communications systems, can readily employ aspects and embodiments of the invention.

A device that a user carried on or about his or her person, that monitored the local air quality and provided early warning of worsening air quality would allow the user to take measures to avoid being exposed to the environment and thereby avoid episodes of compromised or aggravated respiration, and perhaps also eliminate the need to take medications to alleviate such.

Particle counters are typically used in manufacturing or industrial applications to measure particulate quantities in air, gases or liquids. Typically such counters also bin particulates by size. These size bins vary by application and often by instrument. A particle counter has at least one size channel and popular counters can have 6 or more channels. Typically these size channels discriminate pulses based on the pulse height of the incoming signal. The pulse height referring to the peak voltage of the signal. Sometimes there is also rudimentary discrimination of pulse width, often in hardware.

Figure 6:
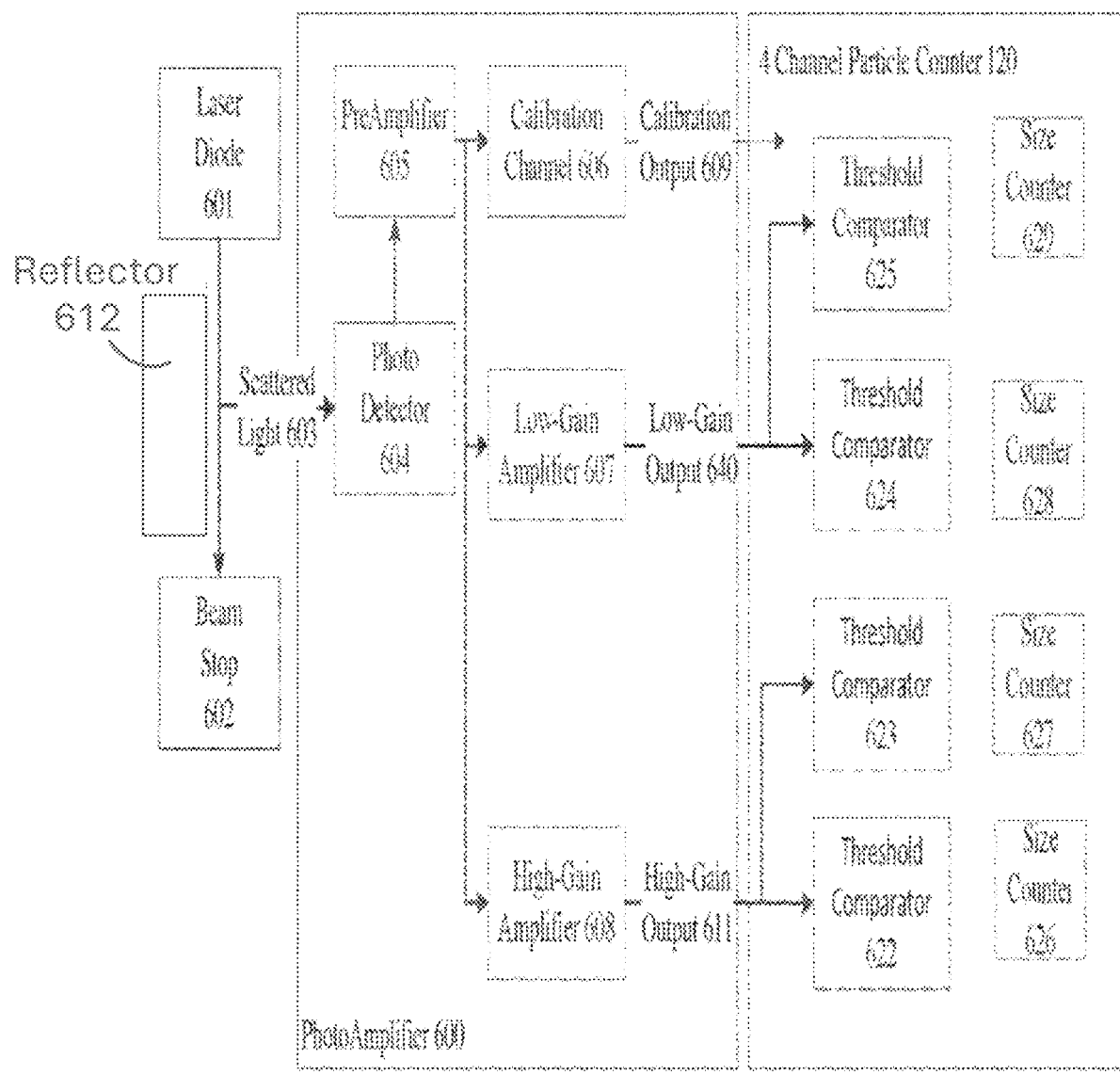
FIG. 6 shows an embodiment of an optical particle counter device.

Referring now to FIG. 6, illustrated is one implementation of a particle counter used in manufacturing or industrial applications. In this example a beam present between the laser diode (601) and the beam stop (602) scatters light (603) as particles cross that beam. Typically the scattered light (603) is focused by a reflector (612) onto the face of a photo-diode (604) on a photo-amplifier board (600). The tiny current in the photo-diode is then pre-amplified, usually by a trans-impedance amplifier (605). The pre-amplified signal is usually available on a calibration channel (606) for use during calibration. The pre-amplifier (605) signal is also sent to one or more amplifiers. In this case there are two, a low-gain channel (607) and a high-gain channel (608).

These amplifiers further increase the signal amplitude and transmit send it, often, to a separate particle counting board (620). On this board the incoming pulse signals are sorted into size bins. In this example there are four channels, two channels (622,623) connected to the high-gain amplifier (611) and two channels (624,625) connected to the low-gain amplifier (610). The threshold comparators (622,623,624, 625) are setup during the calibration phase so that they each channel counts pulses above some threshold. This can be a manual process with manual adjustment of a potentiometer, or a programmatic process where firmware would set a digital potentiometer or digital-to-analog converter. The counter outputs (626,627,628,629) would then be read by microcontroller and displayed to the user.

In certain embodiments, an air quality monitoring system, such as a portable particle detection system, is worn or carried by a user to provide real-time monitoring of the air quality in their local environment as described in U.S. Pat. No. 9,141,094, the entire contents of which is incorporated herein by reference.

Figure 7:
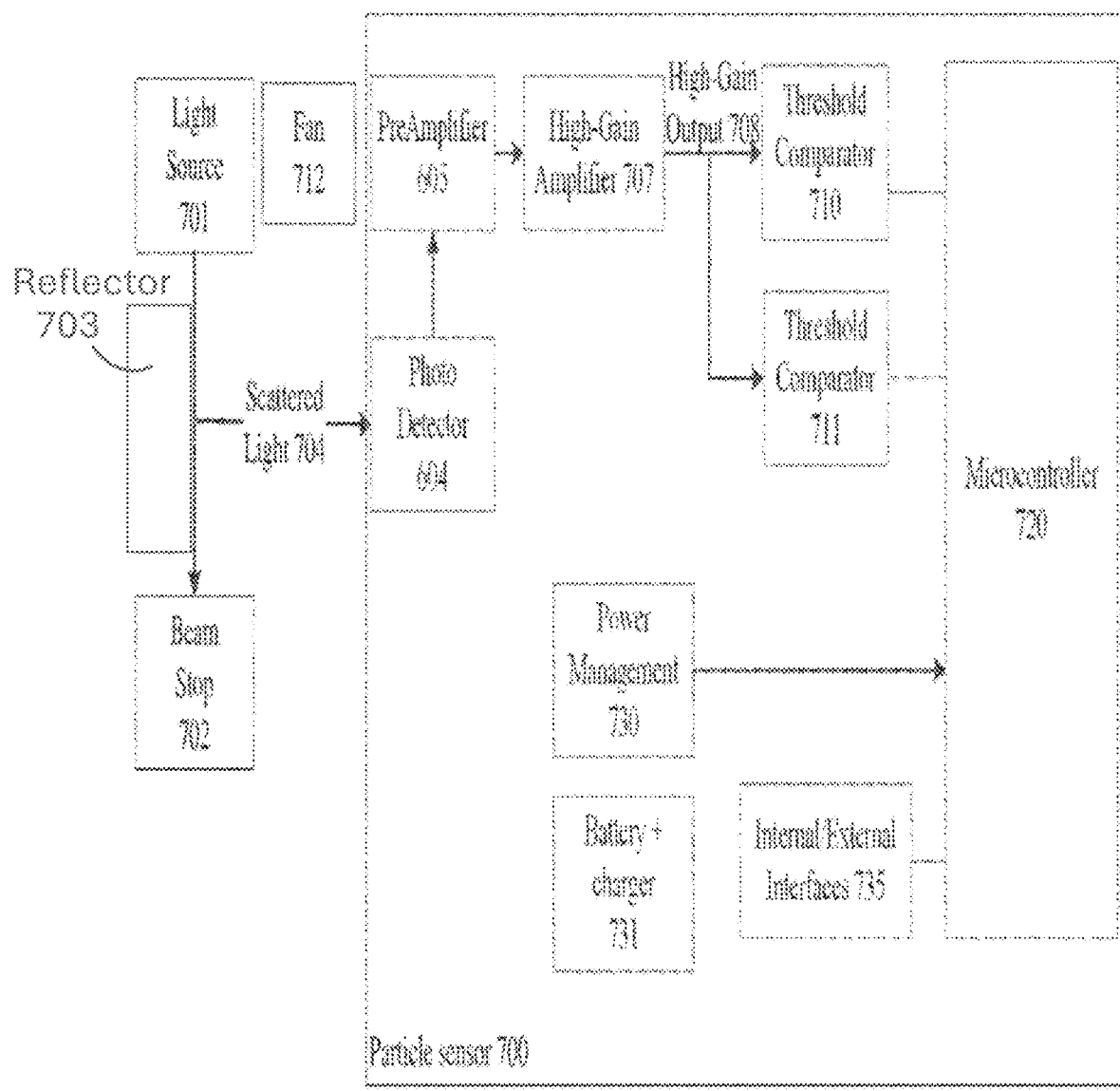
FIG. 7 shown a further embodiment of an optical particle counter device.

Referring now to FIG. 7, illustrated is an embodiment of an air quality monitoring system (700), also referred to as "personal particle counter" or "personal counter" or "personal counter device." Here, air is passed through a light beam generated by a light source (701) where particles scatter light (704). The airstream is generated by a fan or blower (712) or some other air impeller or actuator where air is drawn or pushed into the enclosure and is routed in such a way as to pass through the beam. In certain embodiments, the light source is a laser diode, a light-emitting-diode, or the equivalent. The light is focused by a lens to create a ribbon or beam of light through which the airstream passes, in order to provide controlled scattering of light by particle size. In another implementation, a light blocking system is utilized, in which a beam is presented to a photo-diode and particles obscure the beam as they pass through it, thereby providing the signal.

In the case of a light-scattering system, light scattered by particles in the stream (704) gets collected by a reflector (703) and presented to the photo-detector (705) and the resulting signal is amplified by the pre-amplifier stage (706), such as a trans-impedance amplifier. In some cases a second amplification (707) is utilized and the resulting electrical signal is used to drive one or more threshold comparators (710, 711). The outputs of the threshold comparators (710, 711) is used as inputs to counter channels within the microcontroller (720). These counts are used to determine the quality of the air. In this case there are two separate channels, which can be setup to different counts for particles of different sizes.

The air quality monitoring system (700) is powered locally by a battery (731), which is charged from some external power source. A large number of charging techniques are possible including, but not limited to: an external power connector, power from some external wired interface, wireless (inductive) charging, a solar cell, local charging from energy harvesting means. The battery power is managed locally via the Power Management circuit (730) that provided regulated power to the on-board circuitry (including the analog circuits (amplifiers, comparators, etc.)) and the digital circuitry (microcontroller, internal/external interfaces).

Here, the internal/external user interfaces (735) is communicatively coupled to the threshold comparator. In certain embodiments, the internal/external user interfaces (735) comprise one or more of these non-limiting features: an on-board display, liquid-crystal-display (LCD) or other, to display current air quality status, air-quality over time, cumulative particulate mass, graphs, charts, etc. or other air quality: an on-board memory or a shared memory and shared memory controller to enable high speed streaming of data in real time to an external network and to facilitate handling in real time of received commands from the external network to control sensor operation or robotic movement of a motorized system on which the sensor operates, (volatile or non-volatile) to store or log historic air quality data (for display use or later retrieval and reporting or analysis); an on-board eccentric-rotating-mass (ERM) motor, to provide vibration to alert or interface with user: an on-board audio transducer, to provide sound to alert or interface with user; one or more push-buttons on-board, to interface with user, an on-board wired interface channel for communication with external devices; an on-board wired interface to allow the battery to be charged, and an on-board wireless communications interface channel for communication with external devices.

Figure 8:
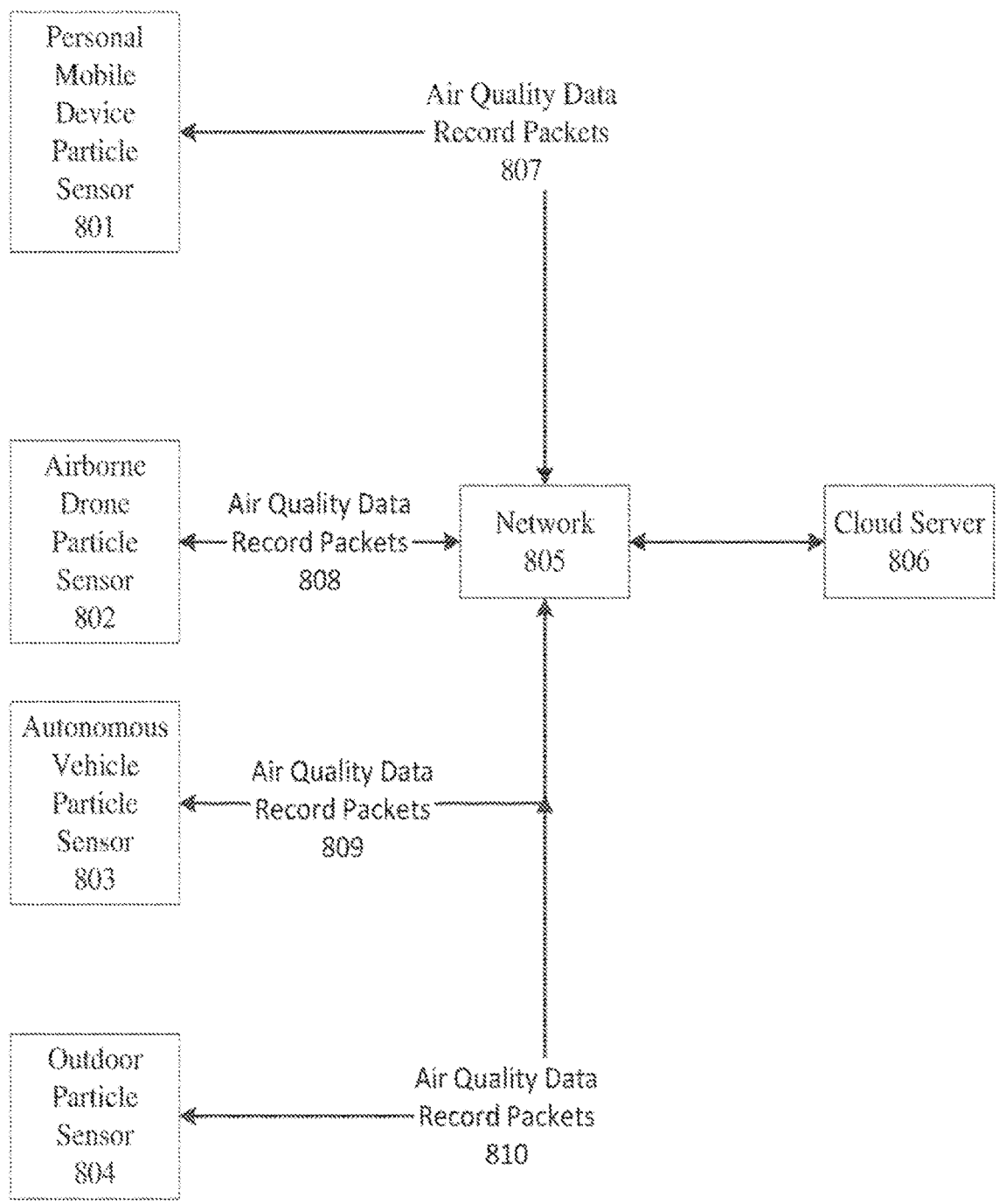
FIG. 8 illustrates a network of sensor devices providing particle count data for mapping of air quality.

Shown in FIG. 8 is a schematic illustration of a networked plurality of geographically dispersed airborne particle sensor devices 801, 802, 803, 804, that can be networked via wired or wireless connection to a communication network 805 as described herein. The network 805 can include connections to a cloud server 806 or system server as described herein to facilitate processing and management of data. The network receives data record packets 807, 808, 809, 810 from respective sensors.

Figure 9:
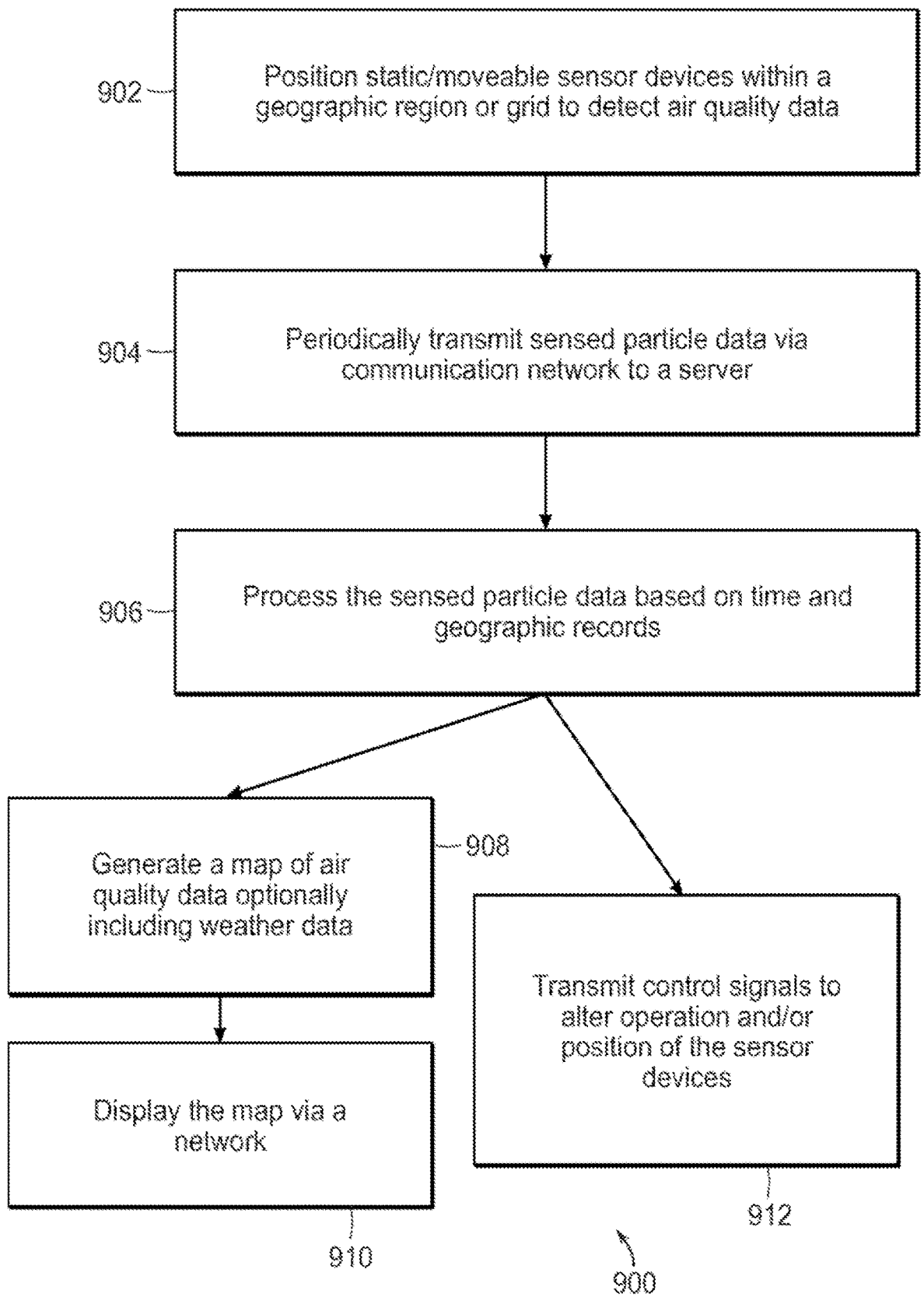
FIG. 9 illustrates a process flow sequence for mapping of air quality data.

Shown in FIG. 9 is a process flow sequence 900 depicting data processing operations for a networked system of geo-located sensor devices positioned 902 within a geographic region or grid in which sensed particle data are transmitted 904 via a communication network to a server and/or computer system to process 906 the data based on time and geographic data records. The system generates a map 908 that can include contemporaneous weather data and subsequently displayed 910. The system also transmits control signals 912 to one or more sensor devices to control operation of the sensor and optionally control sensor movement.

In certain embodiments, a counter includes a multiple sensor block having photo-amplifier sub-assemblies within a single counter instrument as described in U.S. Pat. No. 10,352,844 the entire contents of which is incorporated herein by reference. Each of these blocks can be communicatively coupled, e.g. connected, to a common counter board, or alternatively each of these blocks can have individual counter interface boards which might then provide processed data to a common instrument board having a processor which manages the display, and external interfaces.

In certain embodiments, the airstream is split into multiple segments, each with a respective sensor block. Such an embodiment means that the particle velocity is slowed for each sensor given a fixed sample volume, this means that the system gets more signal per particle and thus can develop a more sensitive instrument (on all channels). The system can use a count comparator to correlate counts between multiple sensors, which allows for failure notification, since one failed sensor will mean a loss of count uniformity, and also for calibration notification, since count uniformity will degrade. This also makes redundancy, as remaining sensors to estimate counts for a failed sensor; and the system can assign different sensors for different size ranges, and thereby provide a sensor with a much larger dynamic range.

In certain embodiments, separate sensor blocks sample different airstreams. For example, instruments with multiple sensors can check that filtration is working as expected. By sampling air from either side of the filter simultaneously, the system can check that particulate counts from two or more sensors reflect a functioning filtered. The system can also check that manufacturing equipment is operating as expected. By sampling air from various areas around a particular piece of equipment, the system can ensure that particulate levels are what is expected. Doing so with a single instrument allows the device to correlate these counts and make decisions that involve more than a single threshold, and allow for an upgrade path for manifold systems that currently share a sensor block and switch airstreams between samples, sharing a single block, which means that there is no continuous sampling of all channels. By replacing this with a counter multiple chambers, the manifold installation could be made continuous, at a lower cost than providing individual instruments for each channel.

Figure 10:
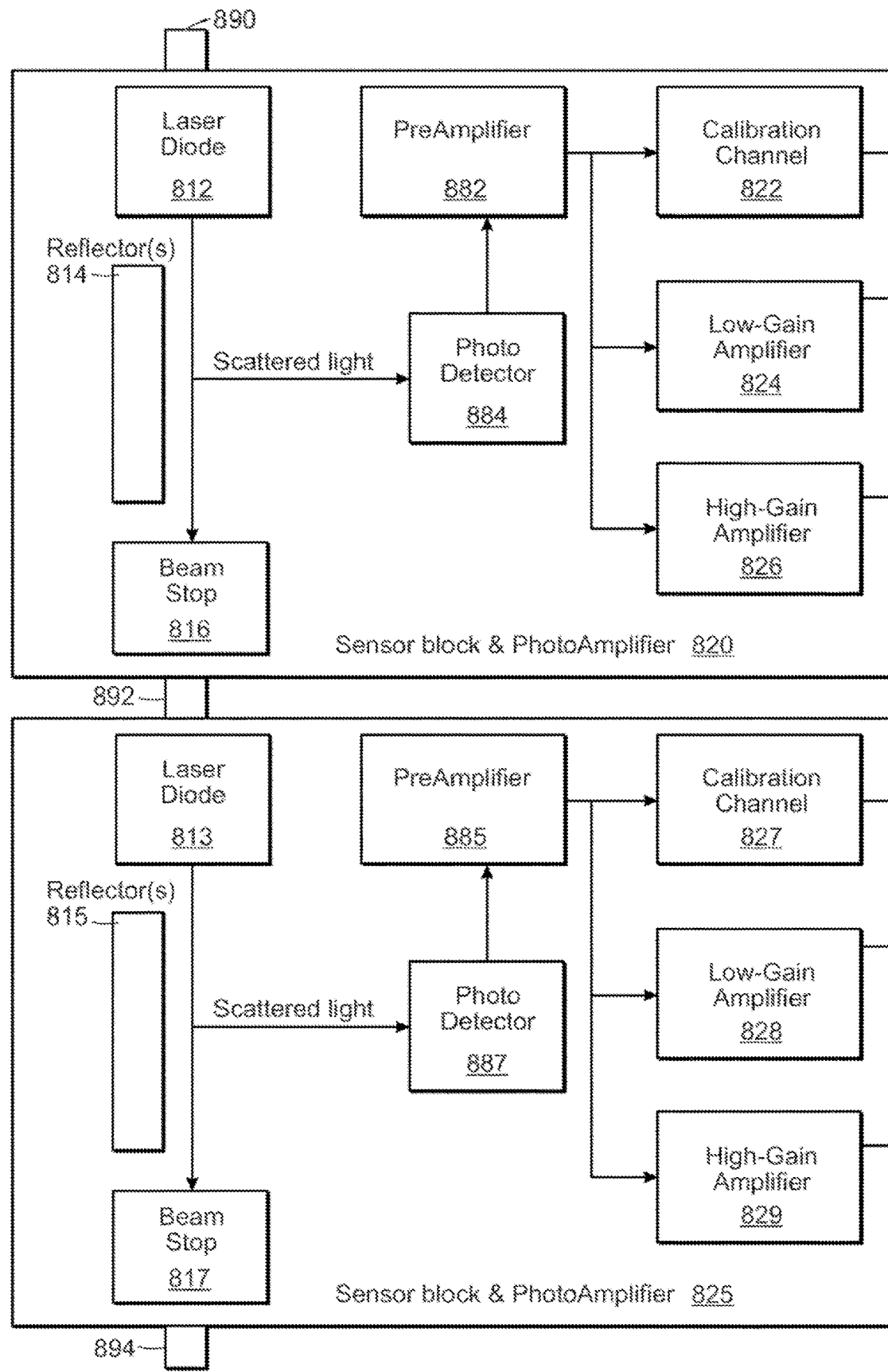
FIG. 10 illustrates a multi-sensor device in accordance with preferred embodiments.
Figure 10:
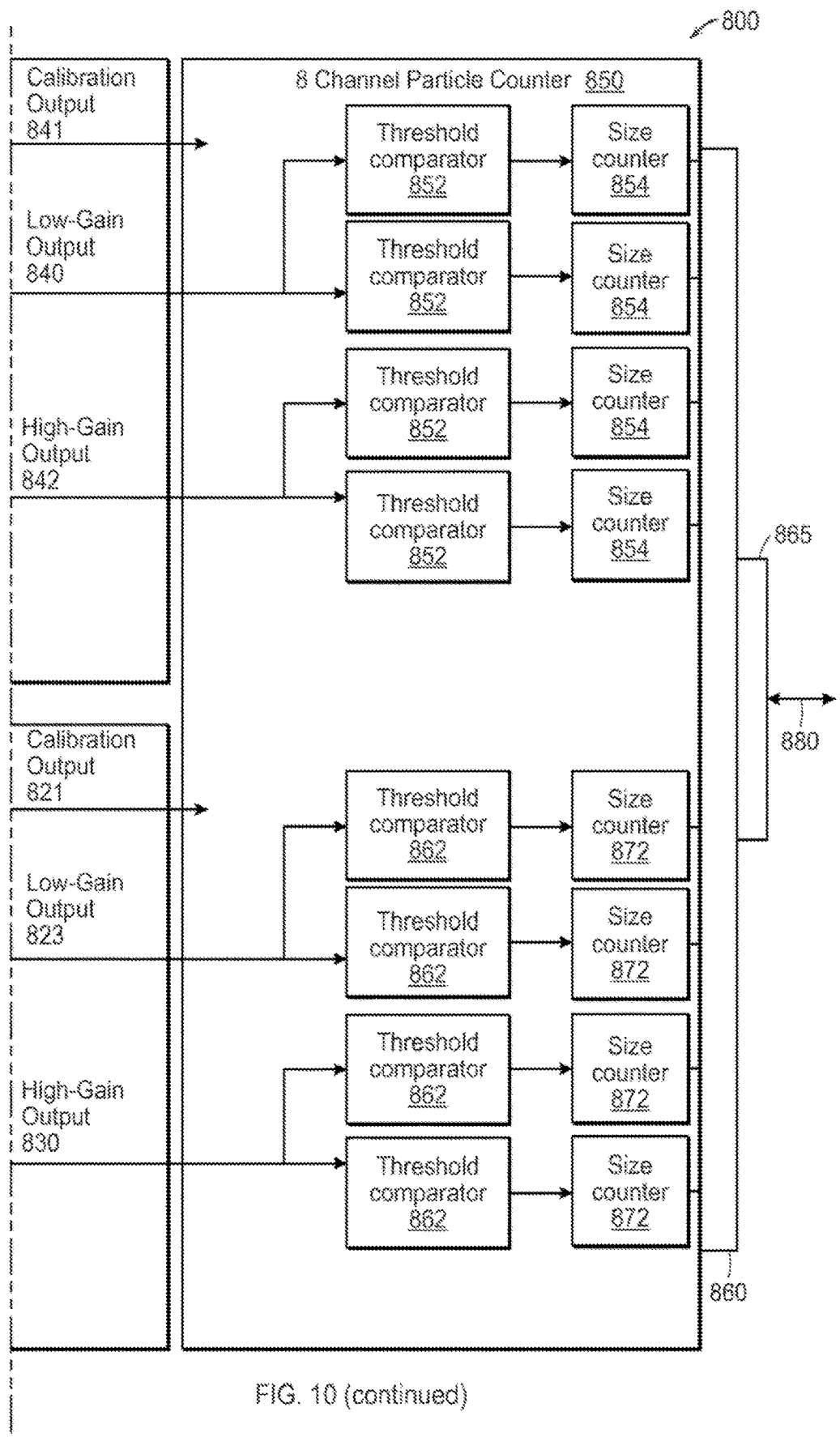

The embodiment of FIG. 10, one such architecture, shown as system 800, provides two or more sensor blocks (820, 825) includes each having gain outputs (840, 842, 823, 830), the two or more sensor blocks (820, 825) being communicatively coupled to a common counter board (850) which implements the threshold comparators (852, 862) and counters (854, 872). Each sensor has a calibration channel (822, 827), low gain (824, 828) and high gain (826, 829) amplifiers generating outputs (841, 821).

Preferred embodiments using multiple sensors (such as two particle counters in series at different wavelengths) as a method to detect a larger dynamic range and determine characteristics about the particle makeup from an overlap area in both operating ranges of the two or more sensors. In FIG. 10 with the sensor inlet 890 on the top and the outlet 894 on the bottom and the optional coupling 892 between the sensor elements 820, 825. Laser 812 with a longer wavelength on the top (660-800 nm for example) and laser 813 with shorter wavelength (300-500 nm for example) on the bottom are notched with reflectors 814, 815 and beam stop 816, 817. Having the two separate cavities with controlled inlets controls the laminarity of the airflow as particulates transit the beams in order to maintain a tight distribution of scattered light by size (size resolution). In this embodiment both sensors are particle counters, with detectors 884, 887 and amplifiers 882, 885 which count every particle transiting each beam and make overall calculations on air quality, for example mass, by calculating the mass of every individual particle and adding these up in order to provide a measure of overall mass. In a further embodiment one of the sensor includes a photometer. Photometers are widely used in outdoor air quality applications (due to the sometimes very large particle concentrations, which can make counting large concentrations problematic for some counters). In the embodiment of FIG. 10 where top particle counter 820 is identical, but the particle counter on the bottom has been replaced by a photometer. In this case the wavelengths of the lasers can be identical or operate at different wavelengths (to increase the ability of detecting smaller particulates). The photometer can measure the aggregate level of scattered light within the cloud illuminated by the laser (as opposed to attempting to capture individual pulses). On board processor 860 and interface 865 controls network communication.

The benefits of this topology are that providing size distribution information to the photometer, the particle mass estimation of the photometer can be adjusted to be much more accurate over a broader range of conditions. If the two sensors ran at different wavelengths then the information from both enables discrimination of the type of particulates which provides the means to more accurately estimate density/refractivity and thereby size and ultimately mass. This can enable operation in extreme environments where the particle counter couldn't accurately process all the particulates due to excessive density (coincidence). In such environments, the particle counter can still provide a reasonable though degraded determination of particle size distribution, which can be used in the calculations within the photometer. This embodiment can be used to dynamically set the baseline for the photometer. One issue with photometers is that the baseline (zero-point) can drift significantly over time with age and temperature of the device. Since the particle counter has a reasonable measure of the baseline, and since the particle counter during normal operation has a reasonably accurate measure of size distribution, the device can therefore predict reasonably well what the photometer output should be. This can be used to adjust the photometer baseline, so that during high-concentration periods where the particle counter might be operating in a degraded capacity, the photometer output would then be much more accurate than it would have been alone. The embodiments of FIG. 10 can be battery powered portable or hand carried as described previously with other embodiments for both mobile and static measurements that can be remotely adjusted or controlled using feedback control software.

Firstly, consider particle counting and estimation of particulate size and mass. An actual particle counter counts 100% of the particles passing through the sensor and the velocity of those particles is tightly controlled so that the amount of light scattered by similarly-sized and similarly refractive and shaped particles is reasonably uniform.

A high-quality particle counter can discriminate actual particles passing through the instrument from background noise in the instrument. ISO 21501-4 (standard used for calibrating particle counters for the cleanroom and manufacturing industries) requires that the instrument have a peak signal-to-noise ratio of at least 2:1. To calculate that, calibration particles of the target size (which have a very uniform size, geometry and refractivity) are un through the instrument and a histogram is created with the peak voltages for all the signals processed by the counter. Each of these voltages is binned by the peak height to give a number of counts for each of the "bins" in the histogram. A signal-to-noise value is what allows an instrument to discriminate real particulates from background system noise. Typically the threshold for that particulate channel can be set at the peak of a histogram so that the instrument counts roughly 50% of all particles of the chosen size.

In addition to the signal-to-noise, ISO21501-4 also requires that the width of at least one calibration size be <15%, essentially this considers regions left and right of the peak to where the counts for each are ~61% of the peak count and then take the voltage at these points and divide the difference from the peak voltage over the peak voltage. The 61% points are selected and the lower threshold is at 0.204 volts which means that the size resolution on this side is 12.1% ((0.232−0.204)/0.232) and the upper threshold is 0.249 volts so that the size resolution on that side is 7.3% ((0.249−0.232)/0.232). The largest of the two size-resolution values is used as the actual size resolution. This size resolution data is a measure of how uniformly the particulates are sized by the instrument, the higher the size resolution figure the more poorly the instrument resolves particles by size.

Once these peaks are generated for the various sizes (each particle size is well separated from each other, in the present instruments, 0.3 um particles are ~250 mv and 0.5 um particles at 1250 mv and so on, the counters are calibrated against, these peaks are recorded as thresholds for these sizes so that when the instrument is running any particles with peaks larger than these thresholds are counted as particles in that size channel.

There are a number of other tests in ISO21501-4 which ensure that the instrument counts accurately and that two instruments manufactured and calibrated by different parties agree on the particulate counts in the same environment.

For a particle counter that passes ISO21501-4 that is placed in an environment looking at room air and the counts in each channel (smaller size channels on the left and larger size channels on the right) a user will typically see a log-type distribution of particulates, where there are many more smaller particles and relatively few very large particles. In many cases, dealing with room air, the particles are NOT uniform in size, shape, density, and refractivity. However, despite the large variance in particle parameters, such instruments typically can accurately estimate particle size and counting them within a calibrated range particle characteristics.

In an example where two instruments were calibrated six months apart that were aspirated against each other looking at the same room air. The two instruments agree on the number of particles of each size in this environment.

The instruments measure and record the raw particle counts for the various channels the user chose. The instrument can then display those particles in various formats: Raw particle counts, concentration or mass.

To calculate concentration, where the sample time and the flow rate are known and both are tightly controlled, based on these the system can figure out the concentration. For example, if the flow rate is 0.1 cfm (cubic-feet/minute) and the air is sampled for 60 seconds, then the device sampled 0.1 cf (cubic feet) and if the device is displaying the concentration in cubic feet the system can simply take the raw counts and multiply by 10. Similarly the system can calculate the concentration in cubic meters, or adjust for different sample times or flow rates.

To calculate mass, the device estimates the average size of the particle in each channel. Since the channel size and the adjacent channel size are known can estimate the average size of the particles in that channel. The device can actually aggregate the actual size of each particle in each channel and arrive at much more accurate estimation of that average size. Once the estimated average size is known, the device then calculates the volume of the particle from the average size (which is its diameter ($V=4/3\pi r3$)) then estimate the density of the particle and the refractivity of the particle. These two last parameters use values that can be adjusted by the user, but the density and refractivity can vary widely based on the particle type (whether it's exhaust (carbon) or road dust, or gypsum, or corn starch, power has a huge impact on these estimates.

For refractivity, highly refractive particles scatter more light and thus appear much larger than poorly refractive particles of the same size and thus might well get placed in a different size bin (more likely if the bins are closely spaced).

If refractivity was constant, but density varied greatly, then there is a potentially significant delta for the actual mass for lighter particulates versus denser particulates, though for in this device they appear the same if it used the same density figure.

In order to compensate for this, the device can allow the user to adjust both the refractivity and density figures to suit the particular application. Typically the instrument runs in parallel with a gravimetric sampler (which pulls a fixed volume of air through a filter, which is then sent out and weighed to arrive at a mass for the particulates in the air), then the user compares this mass to the readings taken with the instrument to arrive at a correction for density or refractivity (since they are factors either can work, or they can be combined into a single correction factor). Presently the device can correct for both density and refractivity on a channel by channel basis. The default settings in the instrument are used for the mass calculation.

The above relates to instruments with a single particle counter, in most cases an optical particle counter using a fixed wavelength laser running in CW (continuous mode). For particle counting there are two types of light scattering that conic to bear: Rayleigh and MIE. Scattering intensity for particles whose size is near the wavelength of the laser is dominated by MIE scattering, and for particles that are significantly smaller than the wavelength, Rayleigh scattering dominates. Since the sky typically has very small particles <200 nm these tend to scatter shorter wavelengths (which is why we see it as blue). If there's a fire or dust in the air, one can see longer wavelengths like red.

During calibration, the thresholds compensate for any non-linearity in scattering efficiency for the various sizes due to the laser wavelength, which eliminates this as an issue during normal operation, though, the measurement still affected by variations in refractivity and density.

If two counters are used in series (or parallel) and if each of the counters used a different wavelengths and were calibrated at those wavelengths with the same particles. Then during normal operation if the two counters are measuring the same air, variations in size distribution can yield useful information about characteristics of the particles.

A series arrangement like the one shown in FIG. 10 samples the same column of air through both sensors and can use a single pump to pull air through both sensors. In this example, the top counter might have a laser in the near IR range like 785 nm while the bottom counter might have a laser in the blue range 405 nm. Top counter can more easily see the larger particles, while lower counter can more easily see the smaller particles.

A parallel arrangement is also possible even with two counters located in the general vicinity even if they weren't within the same instrument. This can apply to two entirely separate instruments but with different wavelengths placed near each other with the data being analyzed or processed in a 3rd location (for example, in some online server collecting and aggregating the data).

If calibration particles of various sizes are run through both these instruments, they agree to a high degree on the sizes of these and bin them nearly identically. However, as the refractivity is varied, and make-up of the particles, is varied the device starts to see significant variations in how these particles are sized and binned in the different counters. These differences can provide a signature provides information as to the refractivity or density of the particulates. With that information, this type of instruments can provide an indication of the particle type(s) and also might dynamically be able to adjust its internal refractivity and density variables to arrive at a more accurate estimation of mass.

Since there are two sensors in series, they can see roughly the same counts in common size channels so the device can more easily detect a sensor failure (if the two sensors didn't agree on the counts in these channels within some acceptable margin). The same is true for sensors in parallel, if they are co-located they see roughly the same air.

The range of the instrument can be extended as the sensors have a significant area of overlap but they can each focus on either end of the range, allowing for an overall greater range and a larger total number of channels. For example, if counter B was setup to see particles from 0.1 um to 1.0 m and counter A was setup to see particles from 0.3 um to 10 um, the instrument has a range from 0.1 um-10 um and the device has more individual channels than a single instrument can provide.

A sensor (or more) can be added and further extend the range or add another variable characterizing the particulate makeup. These do not both have to be optical particle counters. The two sensors can use entirely different modes. For example, the second counter can be an electrometer (which measures particle size based on electric charge). In this case the device analyzes a similar volume of air (or adjust the concentrations based on the volumes to get comparably scaled values) and then use the size distribution of each instrument to arrive at a similar result.

The system can be managed and accessed via an internal 860 or external interface. This interface can be any number of controller designs, from a microcontroller with some type of standard interface like UART, SPI, I2C, UNIO, PMP, etc. to a custom interface like a memory mapped I/O interface for an off-board controller.

Regardless of the actual interface used, an off-board system can be used to setup and access the counter data for local processing, manipulation, display, etc. or to communicate this data to an external system and to receive commands to control operational parameters of the one or more.

Another option can be to have the sensor block have local processing beyond the typical threshold Comparator and Counter implementation, such that pulse-height was measured for each pulse, and optionally other parameters like pulse-width, time-of-arrival, etc. With such local processing allows the creation of intelligent sensors that can have a configurable number of channels, each with configurable thresholds.

In addition, while wireless device 10 uses several embodiments of the method of the invention, the method may be employed by other than a wireless device or a mobile terminal. Moreover, the system and method of embodiments of the invention will be primarily described in conjunction with mobile communications applications. It should be understood, however, that the invention could be utilized in conjunction with a variety of other applications, both in the mobile communications industries and outside of the mobile communications industries.

The wireless device 10 includes an antenna 12 (or multiple antennae) in operable connection or communication with a transmitter 14 and a receiver 16 in accordance with one aspect of the invention. In accordance with other aspects of the present invention, the transmitter 14 and the receiver 16 may be part of a transceiver 15. The wireless device 10 may further include an apparatus, such as a controller 20 or other processing element, which provides signals to and receives audio segments from the transmitter 14 and receiver 16, respectively. The signals include signaling information in accordance with the air interface standard of the applicable cellular system, and also user speech, received data and/or user generated data. In this regard, the wireless device 10 is capable of operating with one or more air interface standards, communication protocols, modulation types, and access types.

By way of illustration, the wireless device 10 is capable of operating in accordance with any of a number of first, second, third and/or fourth-generation communication protocols or the like. For example, the wireless device 10 may be capable of operating in accordance with second-generation (2G) wireless communication protocols IS-136 (time division multiple access (TDMA)), GSM (global system for mobile communication), and IS-95 (code division multiple access (CDMA)), or with third-generation (3G) wireless communication protocols, such as Universal Mobile Telecommunications System (UMTS), CDMA2000, wideband CDMA (WCDMA) and time division-synchronous CDMA (TD-SCDMA), with fourth-generation (4G) wireless communication protocols or the like. As an alternative (or additionally), the wireless device 10 may be capable of operating in accordance with non-cellular communication mechanisms. For example, the wireless device 10 may be capable of communication in a wireless local area network (WLAN) or other communication networks. The wireless device 10 can also have multiple networking capabilities including nomadic wired tethering, local-area-network transceivers (e.g. IEEE802 Wi-Fi), wide-area-network transceivers (IEEE 802.16 WiMAN/WiMAX, cellular data transceivers, (e.g. LTE) and short-range, data-only wireless protocols such as Ultra-wide-band (UWB), Bluetooth, RFID, Near-field-communications (NFC), etc.

It is understood that the apparatus, such as the controller 20, may include circuitry desirable for implementing audio and logic functions of the wireless device 10. For example, the controller 20 may include a digital signal processor device, a microprocessor device, and various analog to digital converters, digital to analog converters, and other support circuits. Control and signal processing functions of the wireless device 10 are allocated between these devices according to their respective capabilities. The controller 20 may also include the functionality to encode and interleave message and data prior to modulation and transmission. The controller 20 can additionally include an internal voice coder, and may include an internal data modem. Further, the controller 20 may include functionality to operate one or more software programs, which may be stored in memory, such as speech recognition programs. For example, the controller 20 may be capable of operating a connectivity program, such as a conventional web browser. The connectivity program may then allow the wireless device 10 to transmit and receive Web content, such as location-based content and/or other web page content, according to a Wireless Application Protocol (WAP), Hypertext Transfer Protocol (HTTP) and/or the like, for example.

The wireless device 10 may also comprise a user interface including an output device such as a conventional earphone or speaker 24, a ringer 22, a camera 23, a microphone 26, a display 28, and at least one user input interface, all of which are coupled to the controller 20. The camera 23 allows the user to capture images and display those images on the display 28. The user input interface, which allows the wireless device 10 to receive data, may include any of a number of devices allowing the wireless device 10 to receive data, such as a keypad 30, a touch display (not shown) or another input device. In embodiments including the keypad 30, the keypad 30 may include the conventional numeric (0-9) and related keys (#, *), and other hard and soft keys used for operating the wireless device 10. Alternatively, the keypad 30 may include a conventional QWERTY keypad arrangement. The keypad 30 may also include various soft keys with associated functions. In addition, or alternatively, the wireless device 10 may include an interface device such as a joystick or another user input interface. The wireless device 10 further includes a battery 34, such as a vibrating battery pack, for powering various circuits that are required to operate the wireless device 10, as well as optionally providing mechanical vibration as a detectable output. Alternatively, or in addition, wireless device 10 may include an energy harvester.

The wireless device 10 may further include a user identity module (UIM) 42. The UIM 42 may be a memory device having a processor built in. The UIM 42 may include, for example, a subscriber identity module (SIM), a universal integrated circuit card (UICC), a universal subscriber identity module (USIM), a removable user identity module (R-UIM), etc. The UIM 42 typically stores information elements related to a mobile subscriber. In addition to the UIM 42, the wireless device 10 may be equipped with memory. For example, the wireless device 10 may include volatile memory 40, such as volatile Random Access Memory (RAM) including a cache area for the temporary storage of data, including captured input audio segments. The wireless device 10 may also include other non-volatile memory 38, which can be embedded and/or may be removable. The non-volatile memory 38 can additionally or alternatively comprise an electrically erasable programmable read only memory (EEPROM), flash memory or the like, such as that available from the SanDisk Corporation of Milpitas, California, or Micron Consumer Products Group Inc. of Milpitas, California. The memories can store any of a number of pieces of information, and data, used by the wireless device 10 to implement the functions of the wireless device 10. For example, the memories can include an identifier, such as an international mobile equipment identification (IMEI) code, capable of uniquely identifying the wireless device 10. Furthermore, the memories may store instructions for determining cell id information. Specifically, the memories may store an application program for execution by the controller 20, which determines an identity of the current cell, i.e., cell identity or cell identification information, with which the wireless device 10 is in communication.

Although not every element of every possible mobile network is shown and described herein, it should be appreciated that the wireless device 10 may be coupled to one or more of any of a number of different networks through a base station. In this regard, the network(s) may be capable of supporting communication in accordance with any one or more of a number of first-generation (1G), second-generation (2G), 2.5G, third-generation (3G). 3.9G, fourth-generation (4G), fifth-generation (5G) mobile communication protocols or the like. For example, one or more of the network(s) can be capable of supporting communication in accordance with 2G wireless communication protocols IS-136 (TDMA), GSM, and IS-95 (CDMA). Also, for example, one or more of the network(s) can be capable of supporting communication in accordance with 2.5G wireless communication protocols GPRS, Enhanced Data GSM Environment (EDGE), or the like. Further, for example, one or more of the network(s) can be capable of supporting communication in accordance with 3G wireless communication protocols such as a UMTS network employing WCDMA radio access technology. Some narrow-band analog mobile phone service (NAMPS), as well as total access communication system (TACS), network(s) may also benefit from embodiments of the invention, as should dual or higher mode mobile stations (e.g., digital/analog or TDMA/CDMA/analog phones).

The wireless device 10 can further be coupled to one or more wireless access points (APs). The APs may comprise access points configured to communicate with the wireless device 10 in accordance with techniques such as, for example, radio frequency (RF), infrared (IrDA) or any of a number of different wireless networking techniques, including WLAN techniques such as IEEE 802.11 (e.g., 802.11a, 802.11b, 802.11g, 802.11n, etc.), world interoperability for microwave access (WiMAX) techniques such as IEEE 802.16, and/or wireless Personal Area Network (WPAN) techniques such as IEEE 802.15, BlueTooth (BT), ultra wideband (UWB) and/or the like. The APs may be coupled to the Internet. The APs can be directly coupled to the Internet. In accordance with other aspects of the invention, the APs are indirectly coupled to the Internet. Furthermore, in one embodiment, the BS may be considered as another AP.

Although preferred embodiments aggregate sensor data from multiple parties into a dynamic geographical map of air quality, the also has applications for private systems as well. Private systems signify single organizations that own all of the sensors and equipment in such a system.

A private system can be deployed for college or corporate campus where mobile and fixed sensors collect data throughout the campus to build an aggregate map of air quality. Mobile sensors can be mounted on drones (or mobile robots, rovers, etc.) that navigate the complex on pre-assigned routes or they could be mounted on campus vehicles or transports (shuttles, golf carts, Segways, etc.). The collected data from these can be aggregated to provide real-time air quality information. If an air quality event occurred (or air quality from a neighboring quarter impinged) on the campus mobile sensors can be tasked to survey the area in question to provide more finely detailed information or to help trace the source of the air quality issue.

In order to meet regulatory and community compliance commitments many large manufacturers must monitor air quality in/around their plant. In order to do so, many deploy large numbers of fixed sensors along the periphery of their installation and monitor these continuously in order to provide a longitudinal record of air quality. In the event of an air quality event by the site this data can be used to track the event and communicate with the community, etc. As with the campus model, these installation would greatly benefit from having mobile sensors. Mobile sensing can result in a dramatic reduction of the number of sensors required to provide fence-line monitoring, while arguably providing much improved performance (since sensors can cover a larger area and be concentrated in an area of interest when such a need presents itself). Mobile sensors can have pre-assigned patrol routes while others (mounted on local transport) can simply opportunistically gather information as personnel travelled around the site using such.

Sensors within the site can be a mixture of fixed and mobile (with geographic data) versions, data from these sensors can be collected and recorded. A dynamic aggregate picture of air quality for the site can be constructed from the data. Models can be used to interpolate intermediate conditions within the map to produce a more continuous map. The aggregate (as well as individual) data can be stored for later analysis or reporting. The collected data can also be used to project air quality into the future based on changes in conditions over time (an application use of machine learning or other model based analysis). During an air quality event, sensors with fixed patrol routes can be assigned modified routes to provide more visibility into areas near and around the source of the issue or controlled dynamically to help identify the actual source.

As will be appreciated, by directly or indirectly connecting the wireless devices 10 to the Internet, the wireless device 10 can communicate with other devices, a computing system, etc., to thereby carry out various functions of the wireless device 10, such as to transmit data, content or the like to, and/or receive content, data or the like from other devices.

As will be apparent to those of skill in the art upon reading this disclosure, each of the aspects described and illustrated herein has discrete components and features, which may be readily separated from or combined with the features and aspects to form embodiments, without departing from the scope or spirit of the invention. Any recited method can be carried out in the order of events recited or in any other order which is logically possible.

Unless defined otherwise, all technical and scientific terms used herein have the same meaning as commonly understood by one of ordinary skill in the art to which this invention belongs. Any methods and materials similar or equivalent to those described herein can also be used in the practice of the invention. Representative illustrative methods and materials are also described.

In accordance with the teaching of the invention a computer and a computing device are articles of manufacture. Other examples of an article of manufacture include: an electronic component residing on a mother board, a server, a mainframe computer, or other special purpose computer each including one or more processors (e.g., a Central Processing Unit, a Graphical Processing Unit, or a microprocessor) that is configured to execute a computer readable program code (e.g., an algorithm, hardware, firmware, and/or software) to receive data, transmit data, store data, or perform methods.

The article of manufacture (e.g., computer or computing device) includes a non-transitory computer readable medium or storage that may include a series of instructions, such as computer readable program steps or code encoded therein. In certain aspects of the invention, the non-transitory computer readable medium includes one or more data repositories. Thus, in certain embodiments that are in accordance with any aspect of the invention, computer readable program code (or code) is encoded in a non-transitory computer readable medium of the computing device.

The processor or a module, in turn, executes the computer readable program code to create or amend an existing computer-aided design using a tool. The term "module" as used herein may refer to one or more circuits, components, registers, processors, software subroutines, or any combination thereof. In other aspects of the embodiments, the creation or amendment of the computer-aided design is implemented as a web-based software application in which portions of the data related to the computer-aided design or the tool or the computer readable program code are received or transmitted to a computing device of a host.

An article of manufacture or system, in accordance with various aspects of the invention, is implemented in a variety of ways: with one or more distinct processors or microprocessors, volatile and/or non-volatile memory and peripherals or peripheral controllers; with an integrated microcontroller, which has a processor, local volatile and non-volatile memory, peripherals and input/output pins; discrete logic which implements a fixed version of the article of manufacture or system; and programmable logic which implements a version of the article of manufacture or system which can be reprogrammed either through a local or remote interface. Such logic could implement a control system either in logic or via a set of commands executed by a processor.

Accordingly, the preceding merely illustrates the various aspects and principles as incorporated in various embodiments of the invention. It will be appreciated that those of ordinary skill in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

Therefore, the scope of the invention, therefore, is not intended to be limited to the various aspects and embodiments discussed and described herein. Rather, the scope and spirit of the invention is embodied by the appended claims.

What is claimed is:

1. An air quality monitoring system comprising:
    a plurality of air quality monitoring instruments dispersed over a geographic area to monitor air quality at different positions within the geographic area and generate an air quality map of the geographic area, wherein each of the plurality of air quality monitoring instruments include at least two air quality sensors with a first light source that emits light at a first wavelength and a second light source that emits light at a second wavelength that is different than the first wavelength, the air quality monitoring instrument being connected to a communication network to communicate particle count data from each of the plurality of air quality monitoring instruments, wherein the at least two air quality sensors include a particle counter having at least four separate particle size channels that each generate particle count data of different sizes over a time period; and
    at least one server in communication with each of the air quality monitoring instruments, wherein air quality information, including a number of particles counted, a date, a time, and a position of an air quality measurement is communicated periodically in a data record from the air quality monitoring instrument performing the air quality measurement using the communication network to the server and, each data record, including the number of particles counted, the date, time, and position information of each air quality measurement is aggregated by the server to create an aggregate data set of air quality data for mapping of a distribution of particles having different sizes over the geographic area.

2. The system of claim 1, wherein the plurality of air quality monitoring instruments are mobile and generate position information that is updated dynamically without user assistance.

3. The system of claim 1, wherein aggregated data is communicated to at least one user in the network.

4. The system of claim 1, wherein the communication network comprises a public network.

5. The system of claim 1, wherein the position information for the air quality sensors is created from triangulation of sensors within a local sensor network, the position information of the particle count data being processed to provide a map of the variation in particle count data over the geographic area.

6. The system of claim 1, wherein at least one additional annotation field is attached to the air quality information.

7. The system of claim 1, wherein at least one additional annotation field is attached to the air quality information and the additional annotation field includes a tag tied to a URL that is accessed by a user.

8. The system of claim 1, wherein the system communicates with a facility management system through the communication network.

9. The system of claim 1, wherein the server provides access to historical data for at least one of: data mining and analysis.

10. The system of claim 1, wherein each of the plurality of air quality monitoring instruments transmits a data record indicating a position of each of the plurality of air quality monitoring instruments that are located indoors or is located outdoors.

11. A system for monitoring air quality comprising:
    a plurality of air quality monitoring instruments to measure air quality at a plurality of different positions over a geographic area to generate an air quality map of the geographic area, each air quality monitoring instrument including:
    a first sensor in an optical particle counter having a first light source that emits light at a first wavelength wherein a first detector measures scattered light from a plurality of particles within an airflow between an inlet and an outlet of the first sensor;
    a second sensor in the optical particle counter having a second light source that emits light at a second wavelength different from the first wavelength wherein a second detector measures scattered light from a plurality of particles within the airflow received from the outlet of the first sensor wherein at least one of the first sensor and the second sensor comprises a photometer wherein the photometer measures an aggregate number of particles with light scattered by a cloud of particles within the airflow wherein the optical particle counter generates a baseline for operation of the photometer; and
    a particle counting circuit that generates particle count data from at least one of the first sensor and the second sensor; and a processor that generates a data field that is transmitted to an external device with a communication network to record a geographic distribution of air quality during a measurement period at the first wavelength and the second wavelength, the data field including at least particle count data, a time, a position and a date corresponding to the particle count data recorded with the first sensor and the second sensor.

12. The system of claim 11 wherein the particle counter further comprises a display that displays the geographic map.

13. The system of claim 12 wherein at least one particle counter is mounted on a drone.

14. The system of claim 11 wherein at least one of the first sensor and the second sensor comprises a particle counter having a plurality of separate particle size channels such that particle data of different particle sizes are mapped for the geographical area.

15. The system of claim 11 wherein the first sensor measures a first particle size range and the second sensor measures a second particle size range.

16. The system of claim 11 wherein the system comprises a portable battery powered optical counter.

* * * * *